United States Patent
Hilgers

(12) 
(10) Patent No.: US 6,610,310 B2
(45) Date of Patent: *Aug. 26, 2003

(54) POLYANIONIC POLYMERS AS ADJUVANTS FOR MUCOSAL IMMUNIZATION

(75) Inventor: Luuk Hilgers, Utrecht (NL)

(73) Assignee: American Cyanamid Company, Madison, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,214

(22) PCT Filed: Oct. 23, 1997

(86) PCT No.: PCT/EP97/05861

§ 371 (c)(1),
(2), (4) Date: Jun. 11, 1999

(87) PCT Pub. No.: WO98/17310

PCT Pub. Date: Apr. 30, 1998

(65) Prior Publication Data

US 2003/0021793 A1 Jan. 30, 2003

(30) Foreign Application Priority Data

Oct. 24, 1996 (GB) ............................................. 9622159

(51) Int. Cl.$^7$ ......................... A61K 47/48; A61K 45/00; A61K 47/00; A61K 39/00; A61K 39/39
(52) U.S. Cl. ............................... 424/280.1; 424/278.1; 424/184.1; 424/78.08; 424/78.17; 424/78.18; 424/78.31; 424/434; 424/435; 514/885
(58) Field of Search ............................ 424/78.08, 78.17, 424/78.18, 78.31, 184.1, 278.1, 280.1, 434, 435; 514/885

(56) References Cited

U.S. PATENT DOCUMENTS 5,026,543 A * 6/1991 Rijke ...................... 424/78.31

FOREIGN PATENT DOCUMENTS

EP          532833 A1 *  3/1993
WO       96/20007    *  7/1996

OTHER PUBLICATIONS

WO 96–20007 A1, Jul. 4, 1996, PTO 99–2576, Vaccine Adjuvants, Luuk Hilgers, et al., United States Patent and Trademark Office, Washington, D.C. Mar. 1999.*

Oka, et al., Guildford, vol. 8, No. 6, Dec. 1990, Influenza vaccine: enhancement of immune response by application of carboxy–vinylpolymer.

* cited by examiner

Primary Examiner—Frederick Krass
Assistant Examiner—Clinton Ostrup
(74) Attorney, Agent, or Firm—Adley F. Mandel; John F. Levis

(57) ABSTRACT

Mucosal adjuvants for vaccines contain water-soluble polyanionic polymers which have anionic constitutional units obtained from acids such as acrylic acid, methacrylic acid, maleic acid, fumaric acid, ethylsulphonic acid, vinylsulphuric acid, vinylsulphonic acid, styrenesulphonic acid, vinylphenylsulphuric acid, 2-methacryloyloxyethane sulphonic acid, 3-methacryloyloxy-2-hydroxypropanesulphonic acid, 3-methacryl amido-3-methylbutanoic acid, acrylamidomethylpropanesulphonic acid, vinylphosphoric acid, 4-vinylbenzoic acid, 3-vinyl oxypropane-1-sulphonic acid, N-vinylsuccinimidic acid, and salts of the foregoing. The polyanionic polymers may further have hydrophobic constitutional repeating units, such as alkylesters, cycloalkylesters, hydroxyalkylesters, ethers, glycols, aromatic groups and salts thereof. The adjuvants containing the polyanionic polymers are used in vaccines for the induction or enhancement of mucosal immune responses.

16 Claims, No Drawings

POLYANIONIC POLYMERS AS ADJUVANTS FOR MUCOSAL IMMUNIZATION

This application is a national stage application filed under 35 U.S.C. 371 of PCT/EP97/05861, filed Oct. 23, 1997.

This invention relates to novel vaccine compositions, processes for the preparation thereof and methods for the use thereof for the mucosal (nonparenteral) immunization of warm blooded animals.

There are two main types of immunity which may provide a host organism protection against disease and/or infection: systemic (or general) immunity which is provided through parenteral vaccination; and mucosal (or local) immunity which is provided through nonparenteral vaccination.

Traditionally, vaccine development has focused on the induction of systemic immunity, including humoral (specific antibodies of IgM or IgG class) and cellular immune responses (activated T lymphocytes, activated macrophages, or others) through the use of parenteral vaccines. Such parenteral vaccines are administered through, inter alia, intramuscular or subcutaneous routes.

While providing systemic immunity through the use of parenteral vaccines and parenteral vaccination has been proven to be effective in establishing protective immunity against many different pathogens, this is not always the case. Numerous examples exist where such immunity has been proven to be wholly or partially ineffective. Furthermore, parenteral vaccines and parenteral vaccination to provide systemic immunity has other disadvantages, such as the need to breach the integrity of the skin of the organism being immunized therewith, difficulty of administration (needing, for example, trained personnel to administer such vaccines), the high grade of purity needed for such vaccines, a lack of establishment of immunity at the site of natural infection, nonprevention of infection and less than complete protection of the organism against both clinical and nonclinical symptoms of the infection as well as against the infection itself. Further, parenteral vaccines can present problems where the effective immunization of immnunocompromised hosts (i.e., young animals with maternal antibodies) is desired.

A multitude of pathogens naturally infect their hosts via the mucosal (e.g. the respiratory, gastrointestinal or genital) tissues. Mucosal (or local) immunity results from the local formation and secretion of antibodies of the IgA class. These antibodies form dimers which can be secreted into the lumen of respiratory, gastro-intestinal or genital organ. Specific IgA antibodies in the lumen are capable of reducing infection by impairing or blocking penetration of the host tissue by the pathogen. Mechanisms known to underly the inhibition of host tissue penetration include: the neutralization of viruses; the complexation with enzymes, toxins or other components produced by the pathogens (resulting in either neutralization of the activity of these components and/or blocking the adsorption of these components); the inhibition of adherence of the pathogens to mucosal surfaces; the suppression of antibody mediated inflammnatory reactions at the mucosal surfaces; and synergism with innate antibacterial factors at the musocal surface.

Mucosal (nonparenteral) vaccines and mucosal vaccination have other additional advantages over parenteral vaccines and parenteral vaccination. These advantages include the elimination of the need to breach the integrity of the skin, tissues or organs of the host, ease of administration, the possibility of employing a low grade of purity, establishment of immunity at the site of natural infection, prevention of penetration of the host tissue by the pathogen, more complete protection of the organism against both clinical and nonclinical symptoms of the infection as well as the infection itself, protection against latency and concomitant induction of mucosal and systemic immunity. Furthermore, mucosal vaccines and mucosal vaccination permit the effective immunization of immunocompromised hosts (i.e., young animals with maternal antibodies).

Thus, it can be seen that, in many cases the use of mucosal (nonparenteral) vaccines, mucosal vaccination and the immunity provided thereby is preferable over the use of parenteral vaccines, parenteral vaccination and the immunity provided thereby.

Depending on various factors, natural or artificial infection with live microorganisms can induce considerable levels of mucosal immunity. These factors include: the route of infection, the nature of the microorganism, the infectious dose involved and the immune status of the host.

However, the administration of killed (non-replicating) antigens gives little or no mucosal immunity. To alleviate this problem, adjuvants are used to increase the immune responses to killed antigens.

The adequate induction of mucosal immunity with killed (non-replicating) antigens requires both the administration of antigen to the mucosae and the use of appropriate adjuvants or antigen presentation systems.

While numerous adjuvants for parenteral vaccines are known, only a few have been shown to be useful in enhancing mucosal immunity. Such adjuvants include the toxin of *Vibrio cholera* (Cholera toxin) or products thereof (Cholera toxin subunit B—CTB), the heat-labile toxin of *E. coli* or products thereof, bacterial toxins or products thereof which are conjugated to antigens, microparticles or microcapsules of different natural or synthetic polymers having antigens incorporated therein, liposomes antigen incorporated therein or liposomes mixed with antigen, lectins, immunostimnulating complexes, muramyldipeptide and derivatives thereof, and cationic polymers (see, "Novel Delivery Systems for Oral Vaccines", CRC Press, London, 1994).

Although well-known, the use of known mucosal adjuvants has been limited. This has been due to several factors, including: the unacceptable risks associated with the detrimental side effects of such adjuvants; problems of insufficient efficacy; the (partial) denaturation of antigens resulting from mechanical and/or chemical treatments which are involved in their preparation procedure; complicated production procedures which are associated therewith; the inconsistency of the production thereof, the high costs of their production; specific immune responses elicited to the adjuvant component; the instability of the adjuvant or the vaccine containing the adjuvant; and the enhancement or activation of nonspecific immune reactions which results from the use thereof.

Thus it can be seen that there remains an urgent need for adjuvants for mucosal vaccines (and, in particular for mucosal vaccines against respiratory diseases, gastro-intestinal diseases and sexually-transmissible diseases) which are safe, inexpensive, easy to produce and to incorporate into mucosal vaccines.

It is a primary object of the present invention to provide mucosal adjuvants capable of inducing or enhancing immune responses to antigens.

It is a further primary object of the present invention to provide mucosal adjuvants for mucosal vaccines (and, in particular, for mucosal vaccines against respiratory diseases, gastro-intestinal diseases and sexually-transmissible diseases) which are safe, inexpensive, easy to produce and easy to incorporate in to such mucosal vaccines in which they are to be employed.

It is a still further primary object of the present invention to provide mucosal vaccines which incorporate such mucosal adjuvants therein for inducing or enhancing immune responses to antigens.

It is a yet further primary object of the present invention to provide methods for inducing or enhancing immune responses to antigens and to provide methods for providing mucosal adjuvants and mucosal vaccines comprised of mucosal adjuvants which are capable of such inducement or enhancement.

The present invention relates to mucosal adjuvants for incorporation into mucosal vaccines and to mucosal vaccines incorporating such adjuvants therein useful for the induction or enhancement of mucosal and/or systemic immune responses to antigens.

Thus, in accordance with the teachings of the present invention, there is provided a mucosal adjuvant for vaccines comprising a water-soluble polyanionic polymer having anionic constitutional repeating units.

The mucosal adjuvants of the present invention are water-soluble polyanionic polymers having anionic constitutional repeating units which may be the same or different repeating units, or polyanionic polymers having anionic constitutional repeating units (same or different) and hydrophobic constitutional repeating units. The polyanionic polymers may be linear (polymers having chemical units which are connected covalently to one or two other constitutional units), or branched (polymers having chemical units which are connected covalently to one or two other constitutional units and occasionally to three or more constitutional units) or reticular (polymers having chemical units which are connected covalently to one or two or three or more other constitutional units) in structure.

As used herein, the following terms have the following meanings:

The term "water soluble", when referring to the polyanionic polymers of the present invention refers to polymers which are soluble in an aqueous phase at a concentration of at least 0.01 gram per liter.

The term "polymer refers to compounds having at least three identical chemical constitutional repeating units, which said units are covalently connected with one another.

The term "constitutional repeating unit refers to the minimal structural unit of a polymer.

The term "homopolymer" refers to polymers consisting of one type of constitutional repeating unit.

The term "heteropolymer" refers to polymers having two or more different constitutional repeating units.

The term "polyanionic polymer" refers to polymers which, when dissolved in an aqueous medium, are negatively charged due to the presence of anionic constitutional repeating units (e.g., units containing sulphate, sulphonate, carboxylate, phosphate and borate groups).

The term "anionic constitutional repeating unit" refers to constitutional repeating units of polymers which are negatively-charged in aqueous medium at physiological conditions.

The term "hydrophobic constitutional repeating unit" refers to constitutional repeating units of polymers which are characterised in that the corresponding monomer is less soluble in an aqueous phase than in an organic solvent [that is to say, the quantity, in weight (in grams), of the monomer that can be dissolved in a fixed volume, in ml, of an aqueous phase is less than the quantity, in weight (in grams), of the monomer that can be dissolved in the same fixed volume, in ml, of the organic solvent].

In the mucosal adjuvants of the present invention the anionic constitutional repeating units of the polyanionic polymer are preferably obtained from acrylic acid, methacrylic acid, maleic acid, fumaric acid, ethylsulphonic acid, vinylsulphuric acid, vinylsulphonic acid, styrenesulphonic acid (vinylbenzenesulphonic acid), vinylphenylsulphuric acid, 2-methacryloyloxyethane sulphonic acid, 3-methacryloyloxy-2-hydroxypropanesulphonic acid, 3-methacryl amido-3-methylbutanoic acid, acrylamidomethylpropanesulfonic acid, vinylphosphoric acid, 4-vinylbenzoic acid, 3-vinyl oxypropane-1-sulphonic acid, N-vinylsuccinimidic acid, and salts of the foregoing.

More preferably, in the mucosal adjuvants of the present invention, the anionic constitutional repeating units of the polyanionic polymer are obtained from acrylic acid, methacrylic acid, maleic acid, fumaric acid, ethylsulphonic acid, vinylsulphuric acid, vinylsulphonic acid, styrenesulphonic acid, and acrylamidomethylpropanesulfonic acid, and salts of the foregoing.

Most preferred in the mucosal adjuvants of the present invention, the anionic constitutional repeating units of the polyanionic polymer are obtained from acrylic acid, methacrylic acid, maleic acid and fumaric acid, vinylsulphonic acid, styrenesulphonic acid, and acrylamidomethylpropanesulfonic acid, and salts of the foregoing.

The mucosal adjuvants of the present invention include polyanionic homopolymers which are preferably obtained from polyacrylic acid, polymethacrylic acid, polymaleic acid, polyfumaric acid, polyethylsulphonic acid, polyvinylsulphuric acid, polyvinylsulphonic acid, polystyrenesulphonic acid (polyvinylbenzenesulphonic acid), polyvinylphenylsulphuric acid, poly 2-methacryloyloxyethanesulphonic acid, poly 3-methacryloyloxy-2-hydroxypropanesulphonic acid, poly 3-methacryl amido-3-methylbutanoic acid, polyacrylamidomethylpropanesulfonic acid, polyvinylphosphoric acid, poly 4-vinylbenzoic acid, poly 3-vinyl oxypropane-1-sulphonic acid, poly N-vinylsuccinimidic acid, and salts of the foregoing.

More preferably, the polyanionic homopolymers are obtained from polyacrylic acid, polymethacrylic acid, polymaleic acid, polyfumaric acid, and salts of any of the fore going.

The mucosal adjuvants of the present invention further include polyanionic heteropolymers having two different (distinct) anionic groups, such as, but not limited to, a carboxylic group and a sulfate or sulfonic group, for example, acrylic acid and any of vinylsulphonic acid, styrenesulphonic acid and acrylamidomethylpropanesulfonic acid.

In a preferred embodiment, the polyanionic polymer of the mucosal adjuvants of the present invention further has hydrophobic constitutional repeating units.

The hydrophobic constitutional repeating units of the polyanionic polymer of the mucosal adjuvants of the present invention are obtained from alkylesters, cycloalkylesters, hydroxyalkylesters, ethers, glycols and aromatic groups and salts of the foregoing.

Preferably, in the mucosal adjuvants of the present invention, the alkylesters are selected from the group consisting of methyl-, ethyl-, propyl-, isopropyl, n-butyl-, isobutyl, sec.butyl-, t-butyl, n-hexyl-, n-octyl-, isooctyl-, 2-ethylhexyl-, n-decyl-, tetradecyl-, vinyl-, allyl- and oleylester.

Preferably, in the mucosal adjuvants of the present invention, the cycloalkylesters are selected from the group consisting of cyclohexyl-, 1-methylcyclohexyl-, 3-vinylcyclohexyl- and 3,3,5-trimethylcyclohexylester.

Preferably, in the mucosal adjuvants of the present invention, the hydroxyalkylesters are selected from the group consisting of 2-hydroxyethyl-, 2-hydroxypropyl-, 3-hydroxypropyl-, 3,4-dihydroxybutyl-, 2-hydroxypenyl- and 2-hydroxyhexylester.

Preferably, in the mucosal adjuvants of the present invention the ethers are selected from the from the group consisting of methoxymethyl, ethoxyethyl, allyloxymethyl, 2-ethoxyethoxymethyl, benzyloxymethyl, cyclohexyloxymethyl, 1-ethoxyethyl, 2-ethoxyethyl, 2-butoxyethyl, methoxymethoxyethyl, methoxyethoxyethyl, 1-butoxypropyl, 1-ethoxybutyl, tetrahydrofurfuryl, furfuryl.

Preferably, in the mucosal adjuvants of the present invention, the glycols are selected from the group consisting of ethylene glycol, 1,2-propanediol, 1,3-propanediol, 1,3-butanediol, 1,4-butanediol, 2,5-dimethyl- 1,6-hexanediol, 1,10-decanediol, diethyleneglycol and triethyleneglycol.

Preferably, in the mucosal adjuvants of the present invention, the aromatic groups are selected from the group consisting of benzyl, phenyl and nonylphenyl.

More preferably, in the mucosal adjuvants of the present invention the hydrophobic constitutional repeating units of the polyanionic polymer are obtained from the group consisting of methyl-, ethyl, propyl, butyl-, pentyl-, hexyl-, heptyl-, octyl-, nonyl-, and decyl- esters of acrylic acid, methacrylic acid, maleic acid, fumaric acid, ethylsulphonic acid, vinylsulphuric acid and styrenesulphonic acid and salts of the foregoing.

Most preferably, in the mucosal adjuvants of the present invention the hydrophobic constitutional repeating units of the polyanionic polymer are obtained from the group consisting of butyl-, pentyl-, hexyl-, heptyl- and octyl- esters of acrylic acid, methacrylic acid, maleic acid and fumaric acid and salts of the foregoing.

Particulaly preferred polyanionic polymers according to the present invention are polyacrylic acid, butyl-polyacrylic acid, poly(acrylate-co-acrylamidomethylpropane sulfonic acid) copolymer (p(A-c-AMPS)), poly(acrylate-co-vinylsulfonate) copolymer (p(A-c-VS)), poly(acrylate-co-vinylbenzenesulfonate) copolymer (p(A-c-VBS)), It is further preferred that in the mucosal adjuvants of the present invention, the molar ratio of hydrophobic constitutional repeating units and anionic constitutional repeating units of the polyanionic polymers of the present invention is between 0 hydrophobic constitutional repeating units per 1 anionic constitutional repeating unit and 0.6 hydrophobic constitutional repeating units per 1 anionic constitutional repeating unit.

More preferably, in the mucosal adjuvants of the present invention, the molar ratio of hydrophobic constitutional repeating units and anionic constitutional repeating units is between 0.02 and 0.60 hydrophobic constitutional repeating unit per 1 anionic constitutional repeating unit (which is from 2 to 60 hydrophobic constitutional repeating units per every 100 anionic constitutional repeating units).

Most preferably, in the mucosal adjuvants of the present invention, the molar ratio of hydrophobic constitutional repeating units and anionic constitutional repeating units is between 0.05 and 0.30 hydrophobic constitutional repeating units per 1 anionic constitutional repeating unit (which is from 5 to 30 hydrophobic constitutional repeating units per every 100 anionic constitutional repeating units).

In another aspect of the present invention, disclosed herein is a mucosal (nonparenteral) vaccine having the mucosal adjuvant (including the polyanionic polymer thereof) of the present invention, wherein the vaccine is administered nonparenterally for the induction of either systemic or mucosal immunity against antigens.

In this aspect, the mucosal vaccine may further be comprised of an antigen or a drug molecule and/or a pharmaceutically-acceptable medium (carrier).

In yet another aspect of (lie present invention, disclosed herein is the use of the water-soluble polyanionic polymers of the present invention for the manufacture or production of mucosal adjuvants for the inducement or enhancement of mucosal or systemic immune responses.

In still another aspect of the present invention, the nonparenteral adjuvant comprised of a polyanionic polymer disclosed herein is administered nonparenterally for the enhancement of either systemic or mucosal immunity against antigens.

The antigen includes live or inactivated viruses, bacteria, fungi, parasites and other microorganisms as well as components or products derived from these microorganisms, products obtained by chemical synthesis capable of eliciting protective immunity, and products obtained by any other means capable of eliciting protective immunity.

Preferred antigens are those capable of eliciting protective immunity to diseases which are infections of the respiratory tract. Examples of such diseases are Newcastle disease virus, infectious bronchitis virus, influenza virus, rhinovirus, parainfluenza virus, adenovirus, Actinobaccilus pleuropneumoniae, Pasteurella multocida, Streptococcus pneumonia, Streptococcus pyogenes, and infections of the gastro-intestinal tract with for example, rotavirus, parvovirus, caronavirus, *E. coli*, Salmonella, Shigella, Yersinia, Campylobactor, Clostridium, Vibrio and Giardia, Entamoeba, and Cryptosporidium.

The polyanionic polymers which may be utilized as the adjuvants of the present invention may be obtained either by the isolation and purification of natural forms thereof or by the synthesis thereof.

Methods to synthesize polyanionic polymers having anionic constitutional repeating units and/or both anionic constitutional repeating units and hydrophobic constitutional repeating units are well known in the state of the art. Such methods include: copolymerisation of anionic and hydrophobic monomers; direct (partial) grafting of appropriate polymers; indirect (partial) grafing of appropriate polymers; and partial hydrolysis of appropriate polymers.

The use of the adjuvants of the present invention in vaccines for mucosal vaccination (immunization) offers various important advantages over those known mucosal adjuvants (and over parenteral vaccines) in that the adjuvants of the present invention are inexpensive, nonimmunogenic, water-soluble, chemically stable, easy to produce and easy to incorporate in the vaccines in which they are intended to be used. Furthermore, these adjuvants are more effective in inducing the desired mucosal immune responses than other adjuvants of which we are aware. Finally, various of the adjuvants described herein are already widely applied in food and pharmaceutical preparations, thereby increasing their acceptability.

The observations relative to the mucosal adjuvants of the present invention, and the mucosal vaccines which incorporate such mucosal adjuvants therein which are illustrated in the examples set forth below are considered unexpected in that: most well-known adjuvants for systemic immunity are not effective in enhancing mucosal immunity; those mucosal adjuvants which are presently employed are moderate or poor adjuvants for systemic immunity; there are crucial differences which exist in the mechanisms that are involved in the induction and development of systemic and mucosal immunity; and the polyanionic polymers disclosed herein are more effective than several of the most-promising mucosal adjuvants presently known.

It is further noted that the polyanionic polymers of the present invention are useful for the induction and/or enhancement of mucosal immune responses to antigens when they are administered either in conjunction with the antigen or separately from the antigen via nonparenteral routes.

The mucosal vaccines having the adjuvants of the present invention are effective for the induction of mucosal immunity, and include both an antigen and an adjuvant, wherein the adjuvant is a water-soluble polyanionic polymer.

The adjuvants of the present invention are solids (for example, are in the form of a powder). If desired, they may be used as such, being applied directly to the surface where an immune response is desired. In such case, being water-soluble, they are solubilized by the mucosal surfaces natural liquids.

Alternatively, the mucosal adjuvants of the present invention may be incorporated into an aqueous solution by being dissolved or incorportade into a liquid medium.

In this regard, the mucosal adjuvants of the present invention may further be incorporated into a vaccine having a liquid medium (such as a pharamaceutically-acceptable carrier). This may be achieved by, for example, being solubilized (as, for example, a powder) in a solution (such as an aqueous solution) containing, for example, an antigen (and/or a drug molecule). Another alternative method of achieving this may be by first dissolving the solid adjuvant in an aqueous phase which may then be either mixed with an aqueous solution of the antigen (and/or drug molecule) or which may then have a lyophilized antigen (and/or drug molecule) solubilized in the solution containing the adjuvant.

Preferably, the vaccines of the present invention are formulated so as to have between 0.01 and 40 mg of the polyanionic polymer (mucosal adjuvant) per ml vaccine.

More preferred, the vaccines of the present invention are formulated so as to have between 0.02 and 20 mg of the polyanionic polymer (mucosal adjuvant) per ml vaccine.

Most preferably the vaccines of the present invention are formulated so as to have between 0.25 and 5 mg of the polyanionic polymer (mucosal adjuvant) per ml vaccine.

The vaccines of the present invention may be applied to mucosal surfaces of animals or humans by nonparenteral routes such as intranasal, oral, oro-nasal, intratracheal and intracloacal. Such application may be made by, for example, the use of liquid aerosols, drinking-water, food, etc.

As used herein, the following terms shall have the meanings which are given therefor:

The term "parenteral immunization" means the administration of a vaccine via the skin by use of a needle or another device using, inter alia one of the following routes: intracutaneous, subcutaneous, intraperitoneal, intramuscular and/or intradermal.

The terms "nonparenteral immunization" and "mucosal immunization" refer to the administration of a vaccine to a mucosal surface by, inter alia one of the following routes: intranasal, oro-nasal, intratracheal, intragastrie, intra-testinal, oral, rectal, intracloacal and/or intravaginal.

The term "systemic immunity" refers to antigen-specific host defense mediated by serum antibodies of IgM or IgG class or by activated T lymphocytes.

The term "mucosal immunity" refers to antigen-specific host defense mediated by antibodies of IgA class present in the host or secreted into the lumen of different organs.

The term "mucosal vaccine" refers to vaccines which are administered via a nonparenteral route to increase mucosal or systemic immune response to an antigen.

The term "mucosal adjuvant" refers to adjuvants which are administered via a nonparenteral route to increase mucosal or systemic immune response to an antigen.

The term "grafted polymer" refers to polymers which are obtained by the addition of chemical groups with a significant effect on chemical, physicochemical or biological properties of the polymer.

The term "copolymer" refers to polymers which are obtained by the polymerisation of two or more distinct monomers in conjunction with one another with significant distinct chemical, physiochemical or biological properties as compared to polymers obtained from either monomer.

The term "liquid medium" refers to mediums of liquid including, but not limited to: aqueous solutions, physiological aqueous solutions, emulsions of the type oil-in-water and suspensions of insoluble salts in an aqueous solution (as well as other types of pharmaceutically-acceptable carriers).

The preferred liquid mediums are aqueous solutions with physiological aqueous solutions being most preferred, although one of the advantages of the present invention is that the vaccine formulation incorporating the mucosal adjuvants disclosed herein need not be physiologic.

EXAMPLE 1

Synthesis of Adjuvant By Copolymerisation of Anionic and Hydrophobic Monomers 540 mmoles of acrylic acid (Merck, Darmstadt, Germany), 60 mmoles of n-butylacrylate (Janssen, Belgium) and 150 ml distilled water were mixed together in a reaction vessel. The resulting reaction mixture was stirred and the pH was adjusted to 4.8 with 10N NaOH. The reaction mixture was then saturated with nitrogen to remove the oxygen present therein.

Five ml of a solution of 88 mM $Na_2S_2O_8$ and five ml of a solution of 175 mM $Na_2S_2O_5$ were then added to the reaction mixture and the reaction mixture was incubated for 6 hours at room temperature with continuous stirring.

The reaction mixture was subsequently dialysed against 1 M NaCl and 0.15 M NaCl using a dialysis membrane with a cut-off of 10 kD (Spectra/por) and then dialysed for at least seven days against distilled water to obtain the polymer. The product was then lyophilized to remove the water therefrom and stored as a dry powder at room temperature.

Analysis of the lyophilized product by NMR (proton NMR with chemical shift calculated from TMS (0 ppm standard) in a device of 500 megacycles (BRUCKER AMX500) using $D_2O$ as solvent at 25° C.) revealed the product to be a polymer containing butylacrylate monomers and acrylate monomers at a molar ratio of 5 butylacrylate monomers per 95 acrylate monomers. Analysis of the molecular weight by gelpermeation chromatography (as described in Vaccine 12, 653–659 (1994)) of the polymer so formed revealed a mean molecular weight of more than 100,000 daltons.

EXAMPLE 2

Synthesis of Adjuvant By Direct (Partial) Grafting of Appropriate Polymers

Respective one gram samples of polyacrylic acid-907 (PAA-907) (CARBOPOL-907 by BFGoodrich, Cleveland, Ohio, USA) were esterified according to the method described by Cohen (J. Polymer Sci. 14, 7–22, 1976) by being solubilized in respective 50 ml samples of pure alkanol (octanol, butanol and methanol, respective) and the solutions were heated to 135° C. Fifty µl of 18 M $H_2SO_4$ were added to each of the solutions and the mixtures were maintained at 135° C. for 10 to 30 minutes. The reactions were then terminated by adding 50 ml of cold distilled water to each reaction mixture and by cooling the reaction mixtures to room temperature. The pH of each reaction mixture was then adjusted to 6 with a 1M NaOH solution and the solvents were removed therefrom by heating the mixtures to 80° C. at low pressure ($10^{-6}$ bar).

The products obtained were then solubilized in distilled water) dialysed for at least seven days using a membrane with a cut-off of 10 kD (Spectra/por) against distilled water and lyophilized to remove the water therefrom.

The compounds obtained in this manner were (grafted polymers) octyl-PAA, butyl-PAA and methyl-PAA. These grafted polymers were analysed by NMR (proton NMR with chemical shift calculated from TMS (0 ppm standard) in a device of 500 megacycles (BRUCKER AMX500) using DMSO as solvent at 120° C.) to determine the esterification grade (mean number of allyl groups per total number of carboxyl groups of the native molecule) thereof. The results of this NMR revealed esterification grades of 16% for octyl-PAA, 16% for butyl-PAA and 15% for methyl-PAA.

EXAMPLE 3

Synthesis of Adjuvant By Indirect (Partial) Grafting of Appropriate Polymers

A solution of 36 grams of PAA-907 (CARBOPOL-907 from BFGoodrich, Ohio, USA) per liter of anhydrous dimethylfornamide was prepared. Fifty ml of this solution was then mixed with 10 ml of anhydrous pyridine to form a PAA-907 solution.

A solution of $CH_3COCl$ at a concentration of 71.2 ml per liter of anhydrous dimethylfornamide was prepared. 7.5 ml of this $CH_3COCl$ solution was added to the PAA-907 solution (molar ratio of 0.3 $CH_3COCl$ per COOH of PAA-907) and the reaction mixture was incubated first for 6 hours at 60° C. and then for 18 hours at room temperature, thereby forming an anhydride between the COOH groups of the PAA-907 and the $CH_3COCl$.

To the mixture so formed, 7 ml of pure, anhydrous 1-butanol was added and the reaction mixture was incubated again for 24 hours at room temperature, whereby the anhydride reacts with the butanol thereby forming butyl-PAA esters and butyl O(C=O)$CH_3$ esters. The product obtained was then dialysed for at least seven days against distilled water using a dialysis membrane with a cut-off of 10 kD (Spectra/por). The polymer was analysed by NMR (proton NMR with chemical shift calculated from TMS (0 ppm standard) in a device of 500 megacycles (BRUCKER AMX500) using DMSO as solvent at 25° C.) which revealed butyl acrylate monomers and acrylate monomers at a molar ratio of 16 butyl acrylate monomers per 84 acrylate monomers.

EXAMPLE 4

Effects of BUTYL-PAA and CTB on Numbers of Anti-NDV IgA and IgG-producing Cells in Lung and Spleen Cell Suspensions Part 1: Preparation of Adjuvant Formulations The butyl-ester of polyacrylic acid BUTYL-PAA), synthesized as described above in Example 2 was then solubilized in various quantities of a phosphate buffer (pH=7.5) containing 15.16 grams of $Na_2HPO_4$ and 2.83 grams of $NaH_4PO_4*2H_2O$ per liter of ultrapure water to produce Butyl-PAA adjuvant solutions (formulations) having concentrations of the Butyl-PAA adjuvant as set forth below in Table 1.

Cholera toxin subunit B (CTB) was obtained from Sigma. The CTB was then solubilized in various quantities of a phosphate buffer (pH=7.5) containing 15.16 grams of $Na_2HPO_4$ and 2.83 grams of $NaH_4PO_4*2H_2O$ per liter of ultrapure water to produce CTB adjuvant solutions (formulations) having concentrations of the CTB adjuvant as set forth below in Table 1.

Part 2: Preparation of the Vaccine Formulations

Newcastle Disease Virus (NDV) strain Lasota (Solyay Duphar, Weesp, The Netherlands) was grown on eggs (following the procedures and under the conditions specified in Wilson, et al., Avian Diseases, 28, 1079–1085 (1984)) and was purified on sucrose gradient and inactivated by β-propiolactone (following the procedures and under the conditions specified in Wilson, et al., Avian Diseases, 28, 1079–1085 (1984)) to give a stock antigen solution. The final concentration of the stock antigen solution contained $10^{8.8}$ median embryo-infective doses per ml before inactivation.

The various vaccine formulations, specified below in Table 1, were then prepared by mixing one volume of the respective various adjuvant formulations, prepared as described above, with one volume of the stock antigen solution.

Finally, a phosphate buffer solution (pH=7.5) was prepared containing 15.16 grams of $Na_2HPO_4$ and 2.83 grams of $NaH_4PO_4*2H_2O$ per liter of ultrapure water. This phosphate buffer solution was used as a control in the experiment below.

Part 3: Immunization of Specimens

Twenty-four female mice (NMRI, Charles River, Germany) were obtained and divided into four groups of six specimens per group.

On day 0, the specimens of each of the four groups were narcotized slightly with ether.

Each of the specimens of one group (Group 1) were then administered respective 40 μl doses of the phosphate buffer solution (pH=7.5) described above in part 1 of this example, which contained neither antigen nor adjuvant, by dropping 20 μl of the said phosphate buffer solution in each nostril of each specimen.

Each of the specimens of a second group (Group 2) were then administered respective 40 μl doses containing a mixture of 20 μl of the pure NDV stock antigen solution and 20 μl of phosphate buffer pH=7.5 (described above) by dropping 20 μl of this mixture in each nostril of each specimen.

Each of the specimens of the remaining two groups (Groups 3 and 4) were then immunized intranasally with respective 40 μl doses of the vaccine formulations (antigen/adjuvant mixtures containing 20 μl of the stock antigen solution and 20 μl of a particular adjuvant formulation), as specified below in Table 1, by dropping 20 μl of a particular vaccine formulation in each nostril of each specimen.

Administration of either the phosphate buffer solution (to the specimens of Group 1), the pure NDV stock antigen solution (to the specimens of Group 2) or the antigen/adjuvant vaccine formulations (to the specimens of Groups 3 and 4) was repeated on day 14 with the same mixture and using the same protocol as described above for day 0.

Part 4: Preparation of Cell Suspensions

On day 21 (week 3) all four groups of specimens were again narcotized with ether and as much blood as possible was collected from each venus plexus thereof.

The specimens were then sacrificed by cervical dislocation and the lungs thereof were carefully removed, so as to avoid the entrance of blood therein. The spleens thereof were also removed.

M199/FCS medium was prepared having 500 ml of M199 medium (Bio Whittaker), 30 ml Fetal calf serum (Gibco BRL), 11.6 ml of a 1 M HEPES solution (Sigma), 7 ml of a 5.6% (w/w) NaHCO3 solution (Analar) and 145 $\mu$l of a gentamycin solution (Gibco BRL).

Within each group, the lungs of two specimens were pooled and treated further as a single sample, yielding 3 samples per group.

The lungs were cut into small pieces and incubated for 2 hours at 37° C. in 5 ml of the M199/FCS medium (described above) which had been further supplemented with collagenase (Sigma) at final concentration of 0.4 mg per ml and $CaCl_2$ at a final concentration of 0.01 M.

The spleen cells were treated in the same manner as the lung cells with the exception that the M199/FCS medium had not been supplemented with either collagenase or $CaCl_2$.

Following incubation the lung pieces were minced through a nylon sieve (Nybold, mesh opening 243 micron) and the cell suspensions were filtered through a nylon sieve (mesh opening 243 micron) and recovered in tubes.

The spleen cells were treated in the same manner, also being recovered in tubes.

The tubes (containing the lung cell suspensions and the spleen cell suspensions) were then centrifiged for 5 minutes at 1,000 RPM (180 g) at 4° C. and the supernatants were removed therefrom. The remaining cell pellets were then resuspended in 2 ml of the M199/FCS medium (described above). The cell suspensions obtained were then added to tubes containing 3 ml Ficoll-paque (Pharmacia) and the tubes were centrifuged for 20 minutes at 18° C. at 2,000 RPM (540 g).

The two lightest fractions resulting from the centrifugation which contained the lymphocytes were then collected in a new series of tubes. The cells were then washed by adding 8 ml of the M199/FCS medium (described above) to about 2 ml of cell suspensions and centrifuged for 5 minutes at 1,000 RPM (180 g) at 4° C. The resulting supernatant was then removed and washing procedure was repeated one more time.

The resulting cell pellets were then resuspended in 2 ml of the M199/FCS medium (described above) and 2 ml of 0.83% (w/v) of $NH_4Cl$ were added to each sample. The cell suspensions were then gently mixed followed by centrifugation for 5 minutes at 1,000 RPM (180 g) at 4° C. The resulting cell pellet was then immediately resuspended in 8 ml of the M199/FCS medium (described above). The tubes were then again centrifuged for 5 minutes at 1,000 RPM (180 g) at 4° C. The supernatant was then removed from the pellets and the cell pellets were resuspended in the M199/FCS medium (described above). The number of living cells were then determined under the microscope with the use of Trypan Blue (SIGMA) and suspensions were adjusted to $2.10^6$ cells per 0.1 ml (100 $\mu$l).

Part 5: Determination of the Number of Antigen Specific Ig-producing Cells in the Cell Suspensions The number of antigen-specific IgA and IgG producing cells in both the lung cell suspensions and the spleen cell suspensions were measured by an ELISA-plaque assay (ELISPOT) as described by Sedwick and Holt (J. Immunol. Meth. 87, 37–44) with the following specifications: the ELISA plates were coated overnight with 50 $\mu$l of a solution of purified, inactivated NDV (strain Lasota, Solyay Duphar) in a carbonate buffer (pH=9.6) containing 0.015 M $Na_2CO_3$ and 0.035 M $NaHCO_3$ at a concentration of about $10^{8.8}$ median embryo-infective dose per ml before inactivation. The plates were subsequently washed 5 times with 0.05% (v/v) Tween 20 (Merck) in phosphate buffered saline (Oxoid; PBS/Tween 20).

100 $\mu$l of the M199/FCS medium (described above) was then added to each well. 100 $\mu$l of the cell suspensions containing 2.106 cells per 100 $\mu$l were then added to the wells of the first column and subsequently serially diluted two-fold in the wells of the same row.

The plates were then covered and incubated for 4 hours at 37° C. in a vibration-free incubator to avoid displacement of the cells settled on the bottom of the wells. Following incubation, demineralized water was injected into each well with sufficient force so as to remove therefrom cells that were adhering thereto. The plates were then subsequently washed five times with PBS/Tween 20 (described above). 50 $\mu$l of goat antimouse IgA conjugated with biotin (Zymed) which had been diluted 500 fold in M199/FCS medium (described above) was then added to each well and the plates were incubated for 2 hours at 37° C.

The plates were then washed 10 times with PBS/Tween 20 (described above) and 50 $\mu$l of streptavidine-alkaline phosphate conjugate (Zymed) which had been previously diluted 500 fold in M199/FCS medium (described above) was then added to each well and the plates were incubated for 18 hours at 4° C.

The plates were then washed 10 times with PBS/Tween 20 (described above). 100 $\mu$l of a warm (40° C.) substrate buffer comprised of 4 volumes of a solution of 1 mM 5-bromo-4-chloro-3-indolyl phosphate (SIGMA) in 1 M 2-amino, 2-methyl, 1-propanol buffer (pH=10.25; Sigma) and 1 volume of a solution of 3 (w/v) % agarose (Sigma) were then added to each well. The plates were then incubated for 2 hours at room temperature and the number of blue spots in the wells containing between 10 and 40 blue spots were counted under the microscope (100× magnification). The number of blue spots per $10^6$ cells were then calculated by dividing the number of spots counted in a well by the number of cells added to that well and multiplying the result by $10^6$.

The respective lung cell suspensions (each suspension being derived from the lungs of two individual specimens) were then tested in triplicate in the ELISPOT. The respective spleen cell suspensions (each suspension being derived from the spleens of two individual specimens) were then tested in triplicate in the ELISPOT. Mean values and the standard error of the mean (SEM) of the three samples of the lung and spleen cell suspensions were then calculated.

The results of such calculations are set forth below in Table 1.

TABLE 1

| Group | Antigen/Adjuvant [mg/ml] | anti-NDV Ig-producing cells/$10^6$ cells 3 weeks following immunization | |
|---|---|---|---|
| | | mean | SEM |
| IgA in the lungs | | | |
| 1 | None/None [0] | 0 | 0 |
| 2 | NDV/None [0] | 2 | 1 |
| 3 | NDV/BUTYL-PAA [10] | 336 | 35 |
| 4 | NDV/CTB [1.0] | 8 | 6 |

TABLE 1-continued

| | | anti-NDV Ig-producing cells/10⁶ cells 3 weeks following immunization | |
|---|---|---|---|
| | Antigen/Adjuvant | | |
| Group | [mg/ml] | mean | SEM |
| IgA in the spleen | | | |
| 1 | None/None [0] | 0 | 0 |
| 2 | NDV/None [0] | 27 | 21 |
| 3 | NDV/BUTYL-PAA [10] | 248 | 226 |
| 4 | NDV/CTB [1.0] | 84 | 23 |
| IgG in the lungs | | | |
| 1 | None/None [0] | 0 | 0 |
| 2 | NDV/None [0] | 0 | 0 |
| 3 | NDV/BUTYL-PAA [1.0] | 112 | 23 |
| 4 | NDDV/CTB [1.0] | 10 | 11 |
| IgG in the spleen | | | |
| 1 | None/None [0] | 0 | 0 |
| 2 | NDV/None [0] | 7 | 2 |
| 3 | NDV/BUTYL-PAA [10] | 64 | 32 |
| 4 | NDV/CTB [1.0] | 8 | 0 |

[mg/ml] is mg of adjuvant/ml of adjuvant solution

EXAMPLE 5

Effects of BUTYL-PAA and SL-CD/squalane/water on Numbers of Anti-NDV IgA-producing Cells in Lung and Spleen Cell Suspensions Part 1: Preparation of Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 2.

A sulpholipo-cyclodextrin/squalane/water (SL-CD/squalane/water) adjuvant formulation was prepared following the protocol described in Hilgers (Vaccine 12, 653–660, 1994) for the sulpholipo-polysucrose/squalane/water formulation with the exception that the sulpholipo-cyclodextrin (SL-CD) was synthesized by adding sulphate and lauroyl groups to beta-cyclodextrin as described for the synthesis of sulpholipo-polysucrose by adding sulphate and lauroyl groups to polysucrose by Hilgers (Immunology, 60, 141–146, 1987) at a molar ratio of 1 mole sulphate, 8 moles lauroyl and 1 mole cyclodextrin. One gram of the SL-CD obtained was then dissolved in two grams of Tween 80. 8 grams of squalane and 390 grams of phosphate buffered saline (PBS) were then added to the SL-CD/Tween 80 solution. The mixture obtained was then emulsified by passing through a Microfluidizer (Microfluidics Inc.) as described for SL-polysucrose/squalane/water by Hilgers (Vaccine 12, 653–660, 1994), thereby forming a SL-CD/squalane/water adjuvant emulsion. The final concentrations of SL-CD, Tween 80 and squalane present in the SL-CD/squalane/water adjuvant formulations used in the respective examples below were 2.5 grams SL-CD per liter of adjuvant emulsion, 5.0 grams of Tween 80 per liter of adjuvant emulsion and 20 grams of squalane per liter adjuvant emulsion.

Part 2: Preparation of the Vaccine Formulations

The Newcastle Disease Virus stock antigen solution and the various vaccine formulations, specified below in Table 2, were prepared as described above in Example 4.

Part 3: Immunization of Specimens

Eighteen female mice (NMRI, Charles River, Germany) were obtained and divided into three groups of six specimens per group.

On day 0, the specimens of each of the three groups were narcotized slightly with ether.

Each of the specimens of one group (Group 1) were then administered respective 40 μl doses containing a mixture of 20 μl of the pure NDV stock antigen solution and 20 μl of phosphate buffer pH=7.5 (described above) by dropping 20 μl of this mixture in each nostril of each specimen.

Each of the specimens of the remaining two groups (Groups 2 and 3) were then immunized intranasally with respective 40 μl doses of the vaccine formulations (antigen/adjuvant mixtures containing 20 μl of the stock antigen solution and 20 μl of a particular adjuvant formulation), as specified below in Table 2, by dropping 20 μl of a particular vaccine formulation in each nostril of each specimen.

Administration of either the pure NDV stock antigen solution (to the specimens of Group 1) or the antigen/adjuvant vaccine formulations (to the specimens of Groups 2 and 3) was repeated on day 14 with the same mixture and using the same protocol as described above for day 0.

Part 4: Preparation of Cell Suspensions

On day 21 (week 3) the three groups of specimens were again narcotized with ether and as much blood as possible was collected from each venus plexus thereof.

The specimens were then sacrificed by cervical dislocation and the lungs thereof were carefully removed, so as to avoid the entrance of blood therein.

In the case of the specimens of Group 1 and Group 2 (as specified in Table 2 below), the spleens thereof were also removed.

Cells suspensions of the lungs and of the spleens were then prepared as described above in Example 4.

Part 5: Determination of the Number of Antigen Specific IgA-producing Cells in the Cell Suspensions The determination of the number of antigen specific IgA-producing cells in the cell suspensions was performed as described above in Example 4, with the exception that the number of antigen specific IgA-producing cells in the spleen cell suspensions of only two samples of Groups 1 and 2 were determined.

The results of such calculations are set forth below in Table 2.

TABLE 2

| | | anti-NDV Ig-producing cells/10⁶ cells 3 weeks following immunization | |
|---|---|---|---|
| | Antigen/Adjuvant | | |
| Group | [mg/ml] | mean | SEM |
| IgA in the lungs | | | |
| 1 | None/None [0] | 19 | 5 |
| 2 | NDV/BUTYL-PAA [10] | 453 | 249 |
| 3 | NDV/SL-CD/squalane/water [2.5] | 23 | 19 |
| IgA in the spleen | | | |
| 1 | None/None [0] | 92 | 59 |
| 2 | NDV/BUTYL-PAA [10] | 324 | 116 |

[mg/ml] is mg of adjuvant/ml of adjuvant solution

EXAMPLE 6

Effects of BUTYL-PAA and PAA-907 on Numbers of Anti-NDV IgA-producing Cells in Lung Cell Suspensions Part 1: Preparation of Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 3.

PAA-907 (CARBOPOL-907; BFGoodrich) was solubilized in various quantities of a phosphate buffer (pH=7.5) containing 15.16 grams of $Na_2HPO_4$ and 2.83 grams of $NaH_4PO_4*2H_2O$ per liter of ultrapure water to produce the PAA-907 adjuvant solutions (formulations) having the varying concentrations of the PAA-907 adjuvant set forth below in Table 3.

Part 2: Preparation of the Vaccine Formulations

The Newcastle Disease Virus stock antigen solution and the various vaccine formulations, specified below in Table 3, were prepared as described above in Example 4.

Part 3: Immunization of the Specimens

Forty-two female mice (NMRI, Charles River, Germany) were obtained and divided into seven groups of six specimens per group.

On day 0, the specimens of each of the seven groups were narcotized slightly with ether.

Each of the specimens of one group (Group 1) were then administered respective 40 µl doses containing a mixture of 20 µl of the pure NDV stock antigen solution and 20 µl of phosphate buffer pH=7.5 (described above) by dropping 20 µl of this mixture in each nostril of each specimen.

Each of the specimens of the remaining six groups (Groups 2, 3, 4, 5, 6 and 7) were then immunized intranasally with respective 40 µl doses of the vaccine formulations (antigen/adjuvant mixtures containing 20 µl of the stock antigen solution and 20 µl of a particular adjuvant formulation), as specified below in Table 3, by dropping 20 µl of a particular vaccine formulation in each nostril of each specimen.

Administration of either the pure NDV stock antigen solution (to the specimens of Group 1) or the antigen/adjuvant vaccine formulations (to the specimens of Groups 2–7) was repeated on day 14 with the same mixture and using the same protocol as described above for day 0.

Part 4: Preparation of Cell Suspensions

On day 21 (week 3) the seven groups of specimens were again narcotized with ether and as much blood as possible was collected from each venus plexus thereof.

The specimens were then sacrificed by cervical dislocation and the lungs thereof were carefully removed, so as to avoid the entrance of blood therein.

Cell suspensions of the lungs were then prepared as described above in Example 4.

Part 5: Determination of the Number of Antigen Specific IgA-producing Cells in the Cell Suspensions The determination of the number of antigen specific IgA-producing cells in the lung cell suspensions was performed as described above in Example 4.

The results of such calculations are set forth below in Table 3.

TABLE 3

| Group | Antigen/Adjuvant [mg/ml] | anti-NDV Ig-producing cells/$10^6$ cells 3 weeks following immunization | |
|---|---|---|---|
| | | mean | SEM |
| IgA in the lungs | | | |
| 1 | NDV/None [0] | 4 | 2 |
| 2 | NDV/BUTYL-PAA [0.5] | 169 | 237 |
| 3 | NDV/BUTYL-PAA [1.7] | 586 | 78 |

TABLE 3-continued

| Group | Antigen/Adjuvant [mg/ml] | anti-NDV Ig-producing cells/$10^6$ cells 3 weeks following immunization | |
|---|---|---|---|
| | | mean | SEM |
| 4 | NDV/BUTYL-PAA [5.0] | 1906 | 2064 |
| 5 | NDV/PAA-907 [0.5] | 80 | 52 |
| 6 | NDV/PAA-907 [1.7] | 120 | 100 |
| 7 | NDV/PAA-907 [5.0] | 118 | 152 |

[mg/ml] is mg of adjuvant/ml of adjuvant solution

EXAMPLE 7

Effects of BUTYL-PAA and PAA-907 on Numbers of Anti-NDV IgA and IgG-producing Cells in Lung and Spleen Cells Suspensions Part 1: Preparation of Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 4.

PAA-907 (CARBOPOL-097; BFGoodrich) and the adjuvant formulations thereof were prepared as described above in Example 6 having the concentrations of the PAA-907 adjuvant set forth below in Table 4.

Part 2: Preparation of the Vaccine Formulations

The Newcastle Disease Virus stock antigen solution and the various vaccine formulations, specified below in Table 4, were prepared as described above in Example 4.

Various graded dilutions of the NDV antigens, i.e. dilutions of 1/12 (standard dose) (v/v), 1/40 (v/v) and 1/120 (v/v) in PBS were then also prepared from the stock antigen solution by the dilution thereof with appropriate quantities of PBS. These dilutions yielded antigen solutions having, respectively, $10^{7.8}$ median embryo-infective doses per ml before inactivation, $10^{7.3}$ median embryo-infective doses per ml before inactivation and $10^{6.8}$ median embryo-infective doses per ml before inactivation.

Part 3: Immunization of the Specimens

Fifty-four female mice (NMRI, Charles River, Germany) were obtained and divided into nine groups of six specimens per group.

On day 0, the specimens of each of the nine groups were narcotized slightly with ether.

Each of the specimens of three groups (Groups 1, 2 and 3) were then administered respective 40 µl doses containing a mixture of 20 µl of the respective pure NDV stock antigen solution dilutions and 20 µl of phosphate buffer pH=7.5 (described above) by dropping 20 µl of this mixture in each nostril of each specimen. The precise dilution of the pure NDV stock antigen solution administered to the specimens of each of the Groups 1, 2 and 3 are set forth below in Table 4.

Each of the specimens of the remaining six groups (Groups 4, 5, 6, 7, 8 and 9) were then immunized intranasally with respective 40 µl doses of the vaccine formulations (antigen/adjuvant mixtures containing 20 µl of the stock antigen solution and 20 µl of a particular adjuvant formulation), as specified below in Table 4, by dropping 20 µl of a particular vaccine formulation in each nostril of each specimen.

Administration of either the pure NDV stock antigen solution (to the specimens of Group 1–3) or the antigen/adjuvant vaccine formulations (to the specimens of Groups 4–9) was repeated on day 14 with the same mixture and using the same protocol as described above for day 0.

Part 4: Preparation of Cell Suspensions

On day 21 (week 3) the specimens were again narcotized with ether and as much blood as possible was collected from each venus plexus thereof.

The specimens were then sacrificed by cervical dislocation and the lungs thereof were carefully removed, so as to avoid the entrance of blood therein.

In the case of the specimens of Groups 1 and 4 (as specified in Table 4 below), the spleens thereof were also removed.

Cell suspensions of the lungs and spleens were then prepared as described above in Example 4.

Part 5: Determination of the Number of Antigen Specific IgA-producing Cells in the Cell Suspensions The determination of the number of antigen specific IgA-producing cells in the lung cell suspensions was performed as described above in Example 4.

The determination of the number of antigen specific IgA-producing cells in the spleen cell suspensions was performed as described above in Example 4, with the exception that the number of antigen specific IgA-producing cells in the spleen cell suspensions of only two samples of Groups 1 and 4 were determined.

The results of such calculations are set forth below in Table 4.

TABLE 4

| Group | Antigen/Adjuvant [mg/ml] | anti-NDV Ig-producing cells/$10^6$ cells 3 weeks following immunization | |
|---|---|---|---|
| | | mean | SEM |
| IgA in the lungs | | | |
| 1 | NDV [1/12]/None [0] | 34 | 14 |
| 2 | NDV [1/40]/None [0] | 7 | 9 |
| 3 | NDV [1/120]/None [0] | 2 | 3 |
| 4 | NDV [1/12]/ BUTYL-PAA [2.5] | 181 | 64 |
| 5 | NDV [1/40]/ BUTYL-PAA [2.5] | 19 | 27 |
| 6 | NDV [1/120]/ BUTYL-PAA [2.5] | 3 | 3 |
| 7 | NDV [1/12]/ PAA-907 [2.5] | 83 | 41 |
| 8 | NDV [1/40]/ PAA-907 [2.5] | 33 | 38 |
| 9 | NDV [1/120]/ PAA-907 [2.5] | 0 | 0 |
| IgA in the spleen | | | |
| 1 | NDV [1/12]/None [0] | 3 | 1 |
| 4 | NDV [1/12]/None [0] | 25 | 1 |

[mg/ml] is mg of adjuvant/ml of adjuvant solution

EXAMPLE 8

Effects of BUTYL-PAA and PAA-907 on Numbers of Anti-NDV IgA-producing Cells in Lung Cell Suspensions Part 1: Preparation of Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 5.

PAA-907 (CARBOPOL-097; BFGoodrich) and the adjuvant formulations thereof were prepared as described above in Example 6 having the concentrations of the PAA-907 adjuvant set forth below in Table 5.

Part 2: Preparation of the Vaccine Formulations

The Newcastle Disease Virus stock antigen solution and the various vaccine formulations, specified below in Table 5, were prepared as described above in Example 4.

Part 3: Immunization of the Specimens

Forty-two female mice (NMRI, Charles River, Germany) were obtained and divided into seven groups of six specimens per group.

On day 0, the specimens of each of the seven groups were narcotized slightly with ether.

Each of the specimens of one group (Group 1) were then administered respective 40 μl doses containing a mixture of 20 μl of the pure NDV stock antigen solution and 20 μl of phosphate buffer pH=7.5 (described above) by dropping 20 μl of this mixture in each nostril of each specimen.

Each of the specimens of the remaining six groups (Groups 2, 3, 4, 5, 6 and 7) were then immunized intranasally with respective 40 μl doses of the vaccine formulations (antigen/adjuvant mixtures containing 20 μl of the stock antigen solution and 20 μl of a particular adjuvant formulation), as specified below in Table 5, by dropping 20 μl of a particular vaccine formulation in each nostril of each specimen.

Administration of either the pure NDV stock antigen solution (to the specimens of Group 1) or the antigen/adjuvant vaccine formulations (to the specimens of Groups 2–7) was repeated on day 14 with the same mixture and using the same protocol as described above for day 0.

Part 4: Preparation of Cell Suspensions

On day 21 (week 3) the specimens were again narcotized with ether and as much blood as possible was collected from each venus plexus thereof.

The specimens were then sacrificed by cervical dislocation and the lungs thereof were carefully removed, so as to avoid the entrance of blood therein.

Cell suspensions of the lung cells were then prepared as described above in Example 4.

Part 5: Determination of the Number of Antigen Specific IgA-producing Cells in the Cell Suspensions The determination of the number of antigen specific IgA-producing cells in the lung cell suspensions was performed as described above in Example 4 with the exception that the number of antigen specific IgA-producing cells in the lung cell suspensions of only two samples of Group 3 were determined. The results of such calculations are set forth below in Table 5.

TABLE 5

| Group | Antigen/Adjuvant [mg/ml] | anti-NDV Ig-producing cells/$10^6$ cells 3 weeks following immunization | |
|---|---|---|---|
| | | mean | SEM |
| IgA in the lungs | | | |
| 1 | NDV/None [0] | 39 | 29 |
| 2 | NDV/BUTYL-PAA [0.5] | 60 | 32 |
| 3 | NDV/BUTYL-PAA [1.7] | 369 | 240 |
| 4 | NDV/BUTYL-PAA [5.0] | 115 | 72 |
| 5 | NDV/PAA-907 [0.5] | 38 | 17 |
| 6 | NDV/PAA-907 [1.7] | 432 | 472 |
| 7 | NDV/PAA-907 [5.0] | 94 | 75 |

[mg/ml] is mg of adjuvant/ml of adjuvant solution

EXAMPLE 9

Effects of BUTYL-PAA, PAA-907, PAA-934PH, Al(OH)$_3$, Liposomes and CTB on Numbers of Anti-NDV IgA-producing Cells in Lung and Spleen Cell Suspensions Part 1: Preparation of Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 6.

PAA-907 (CARBOPOL-907; BFGoodrich) and the adjuvant formulations thereof were prepared as described above in Example 6 having the concentrations of the PAA-907 adjuvant set forth below in Table 6.

CTB and the adjuvant formulations thereof were prepared as described above in Example 4 having the concentrations of the CTB adjuvant set forth below in Table 6.

PAA-934PH (CARBOPOL-934PH; BFGoodrich) was solubilized in various quantities of a phosphate buffer (pH=7.5) containing 15.16 grams of Na$_2$HPO$_4$ and 2.83 grams of NaH$_4$PO$_4$*2H$_2$O per liter of ultrapure water to produce PAA-934PH adjuvant solutions (formulations) having the varying concentrations of the PAA-934PH adjuvant set forth below in Table 6.

Liposomes consisting of egg-yolk phosphatidylcholine (Sigma), cholesterol (Sigma) and cetylphosphate (Sigma) in a molar ratio of 4:5:1, respectively, were prepared as described by de Haan et al. (Vaccine 13, 155–162, 1995). These liposomes were then suspended in various quantities of a phosphate buffer (pH=7.5) containing 15.16 grams of Na$_2$HPO$_4$ and 2.83 grams of NaH$_4$PO$_4$*2H$_2$O per liter of ultrapure water to produce liposome adjuvant suspensions (formulations) having the varying concentrations of the liposome adjuvant set forth below in Table 6.

Al(OH)$_3$ (SUPERFOS) was suspended in various quantities of a phosphate buffer (pH=7.5) containing 15.16 grams of Na$_2$HPO$_4$ and 2.83 grams of NaH$_4$PO$_4$*2H$_2$O per liter of ultrapure water to produce Al(OH)$_3$ adjuvant suspensions (formulations) having the varying concentrations of the Al(OH)$_3$ adjuvant set forth below in Table 6.

Part 2: Preparation of the Vaccine Formulations

The Newcastle Disease Virus stock antigen solution and the various vaccine formulations, specified below in Table 6, were prepared as described above in Example 4.

Part 3: Immunization of the Specimens

Forty-two female mice (NMRI, Charles River, Germany) were obtained and divided into seven groups of six specimens per group.

On day 0, the specimens of each of the seven groups were narcotized slightly with ether.

Each of the specimens of one group (Group 1) were then administered respective 40 µl doses containing a mixture of 20 µl of the pure NDV stock antigen solution and 20 µl of phosphate buffer pH=7.5 (described above) by dropping 20 µl of this mixture in each nostril of each specimen.

Each of the specimens of the remaining six groups (Groups 2, 3, 4, 5, 6 and 7) were then immunized intranasally with respective 40 µl doses of the vaccine formulations (antigen/adjuvant mixtures containing 20 µl of the stock antigen solution and 20 µl of a particular adjuvant formulation), as specified below in Table 6, by dropping 20 µl of a particular vaccine formulation in each nostril of each specimen.

Administration of either the pure NDV stock antigen solution (to the specimens of Group 1) or the antigen/adjuvant vaccine formulations (to the specimens of Groups 2–7) was repeated on day 14 with the same mixture and using the same protocol as described above for day 0.

Part 4: Preparation of Cell Suspensions

On day 21 (week 3) the specimens were again narcotized with ether and as much blood as possible was collected from each venus plexus thereof.

The specimens were then sacrificed by cervical dislocation and the lungs thereof were carefully removed, so as to avoid the entrance of blood therein.

In the case of the specimens of Group 1 and Group 2 (as specified in Table 6 below), the spleens thereof were also removed.

Cell suspensions of the lungs and spleen were then prepared as described above in Example 4.

Part 5: Determination of the Number of Antigen Specific IgA-producing Cells in the Cells Suspensions The determination of the number of antigen specific IgA-producing cells in the lung cell suspensions was performed as described above in Example 4.

The determination of the number of antigen specific IgA-producing cells in the spleen cell suspensions was performed as described above in Example 4, with the exception that the number of antigen specific IgA-producing cells in the spleen cell suspensions of only two samples of Groups 1 and 2 were determined.

The results of such calculations are set forth below in Table 6.

TABLE 6

| | | anti-NDV Ig-producing cells/10$^6$ cells 3 weeks following immunization | |
|---|---|---|---|
| | Antigen/Adjuvant | | |
| Group | [mg/ml] | mean | SEM |
| IgA in the lungs | | | |
| 1 | NDV/None [0] | 10 | 6 |
| 2 | NDV/BUTYL-PAA [2.5] | 72 | 34 |
| 3 | NDV/PAA-907 [2.5] | 65 | 41 |
| 4 | NDV/PAA-934PH [2.5] | 156 | 147 |
| 5 | NDV/Al(OH)$_3$ [2.5] | 6 | 2 |
| 6 | NDV/Liposomes [0.5] | 16 | 19 |
| 7 | NDV/CTB [0.5] | 29 | 16 |
| IgA in the spleen | | | |
| 1 | NDV/None [0] | 11 | 6 |
| 2 | NDV/BUTYL-PAA [2.5] | 36 | 8 |

[mg/ml] is mg of adjuvant/ml of adjuvant solution

EXAMPLE 10

Effects of BUTYL-PAA, PAA-907, PAA-934PH, Al(OH)$_3$, Liposomes and CTB on Numbers of Anti-NDV IgA-producing Cells in Lung and Spleen Cell Suspensions Part 1: Preparation of the Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 7.

PAA-907 (CARBOPOL-097; BFGoodrich) and the adjuvant formulations thereof were prepared as described above in Example 6 having the concentrations of the PAA-907 adjuvant set forth below in Table 7.

CTB and the adjuvant formulations thereof were prepared as described above in Example 4 having the concentrations of the CTB adjuvant set forth below in Table 7.

PAA-934PH (CARBOPOL-934PH; BFGoodrich) and the adjuvant formulations thereof, liposome and the adjuvant formulations thereof and Al(OH)$_3$ (SUPERFOS) and the adjuvant formulations thereof were all prepared as described above in Example 9 having the concentrations of the respective said adjuvants, set forth below in Table 7.

Part 2: Preparation of the Vaccine Formulations

The Newcastle Disease Virus stock antigen solution and the various vaccine formulations, specified below in Table 7, were prepared as described above in Example 4.

Part 3: Immunization of the Specimens

Forty-two female mice (NMRI, Charles River, Germany) were obtained and divided into seven groups of six specimens per group.

On day 0, the specimens of each of the seven groups were narcotized slightly with ether.

Each of the specimens of one group (Group 1) were then administered respective 40 μl doses containing a mixture of 20 μl of the pure NDV stock antigen solution and 20 μl of phosphate buffer pH=7.5 (described above) by dropping 20 μl of this mixture in each nostril of each specimen.

Each of the specimens of the remaining six groups (Groups 2, 3, 4, 5, 6 and 7) were then immunized intranasally with respective 40 μl doses of the vaccine formulations (antigen/adjuvant mixtures containing 20 μl of the stock antigen solution and 20 μl of a particular adjuvant formulation), as specified below in Table 7, by dropping 20 μl of the mixture in each nostril of each specimen.

Administration of either the pure NDV stock solution (to the specimens of Group 1) or the antigen/adjuvant vaccine formulations (to the specimens of Groups 2–7) was repeated on day 14 with the same mixture and using the same protocol as described above for day 0.

Part 4: Preparation of Cell Suspensions

On day 21 (week 3) the specimens were again narcotized with ether and as much blood as possible was collected from each venus plexus thereof.

The specimens were then sacrificed by cervical dislocation and the lungs thereof were carefully removed, so as to avoid the entrance of blood therein.

In the case of the specimens of Group 1 and Group 2 (as specified in Table 7 below), the spleens thereof were also removed.

Cell suspensions of the lungs and spleens were then prepared as described above in Example 4.

Part 5: Determination of the Number of Antigen Specific IgA-producing Cells in the Cell Suspensions The determination of the number of antigen specific IgA-producing cells in the lung cell suspensions was performed as described above in Example 4, with the exception that the number of antigen specific IgA-producing cells in the lung cell suspensions of only two samples of Groups 1 were determined.

The determination of the number of antigen specific IgA-producing cells in the spleen cell suspensions was performed as described above in Example 4, with the exception that the number of antigen specific IgA-producing cells in the spleen cell suspensions of only two samples of Groups 1 and 2 were determined.

The results of such calculations are set forth below in Table 7.

TABLE 7

| Group | Antigen/Adjuvant [mg/ml] | anti-NDV Ig-producing cells/$10^6$ cells 3 weeks following immunization mean | SEM |
|---|---|---|---|
| IgA in the lungs | | | |
| 1 | NDV/None [0] | 2 | 0 |
| 2 | NDV/BUTYL-PAA [2.5] | 202 | 300 |
| 3 | NDV/PAA-907 [2.5] | 12 | 1 |
| 4 | NDV/PAA-934PH [2.5] | 126 | 97 |
| 5 | NDV/$Al(OH)_3$ [2.5] | 8 | 14 |
| 6 | NDV/Liposomes [0.5] | 11 | 14 |
| 7 | NDV/CTB [0.5] | 62 | 32 |
| IgA in the spleen | | | |
| 1 | NDV/None [0] | 14 | 3 |
| 2 | NDV/BUTYL-PAA [2.5] | 21 | 7 |

[mg/ml] is mg of adjuvant/ml of adjuvant solution

EXAMPLE 11

Effects of BUTYL-PAA, PAA-907, PAA-934PH, Al $(OH)_3$, Liposomes and CTB on Numbers of Anti-NDV IgA-producing Cells in Lung and Spleen Cell Suspensions Part 1: Preparation of Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 8.

PAA-907 (CARBOPOL-907; BFGoodrich) and the adjuvant formulations thereof were prepared as described above in Example 6 having the concentrations of the PAA-907 adjuvant set forth below in Table 8.

CTB and the adjuvant formulations thereof were prepared as described above in Example 4 having the concentrations of the CTB adjuvant set forth below in Table 8.

PAA-934PH (CARBOPOL-934PH; BFGoodrich) and the adjuvant formulations thereof, liposome and the adjuvant formulations thereof and $Al(OH)_3$ (SUPERFOS) and the adjuvant formulations thereof were all prepared as described above in Example 9 having the concentrations of the respective said adjuvant set forth below in Table 8.

Part 2: Preparation of the Vaccine Formulations

The Newcastle Disease Virus stock antigen solution and the various vaccine formulations, specified below in Table 8, were prepared as described above in Example 4.

Part 3: Immunization of the Specimens

Forty-two female mice (NMRI, Charles River, Gerrmany) were obtained and divided into seven groups of six specimens per group.

On day 0, the specimens of each of the seven groups were narcotized slightly with ether.

Each of the specimens of one group (Group 1) were then administered respective 40 μl doses containing a mixture of 20 μl of the pure NDV stock antigen solution and 20 μl of phosphate buffer pH=7.5 (described above) by dropping 20 μl of this mixture in each nostril of each specimen.

The specimens of the remaining seven groups (Groups 2, 3, 4, 5, 6 and 7) were then immunized intranasally with respective 40 μl doses of the vaccine formulations (antigen/adjuvant mixtures containing 20 μl of the stock antigen solution and 20 μl of a particular adjuvant formulation), as specified below in Table 8, by dropping 20 µl of the mixture in each nostril of each specimen.

Administration of either the pure NDV stock antigen solution (to the specimens of Group 1) or the antigen/adjuvant vaccine formulations (to the specimens of Groups 2–7) was repeated on day 14 with the same mixture and using the same protocol as described above for day 0.

Part 4: Preparation of Cell Suspensions

On day 21 (week 3) the specimens were again narcotized with ether and as much blood as possible was collected from each venus plexus thereof.

The specimens were then sacrificed by cervical dislocation and the lungs thereof were carefully removed, so as to avoid the entrance of blood therein.

In the case of the specimens of Group 1 and Group 2 (as specified in Table 8 below), the spleens thereof were also removed.

Cell suspensions of the lungs and the spleens were then prepared as described above in Example 4.

Part 5: Determination of the Number of Antigen Specific IgA-producing Cells in the Cells Suspensions The determination of the number of antigen specific IgA-producing cells in the lung cells suspensions was performed as described above in Example 4.

The determination of the number of antigen specific IgA-producing cells in the spleen cell suspensions was performed as described above in Example 4, with the exception that the number of antigen specific IgA-producing cells in the spleen cell suspensions of only two samples of Groups 1 and 2 were determined.

The results of such calculations are set forth below in Table 8.

TABLE 8

| Group | Antigen/Adjuvant [mg/ml] | anti-NDV Ig-producing cells/$10^6$ cells 3 weeks following immunization | |
|---|---|---|---|
| | | mean | SEM |
| IgA in the lungs | | | |
| 1 | NDV/None [0] | 4 | 1 |
| 2 | NDV/BUTYL-PAA [2.5] | 107 | 77 |
| 3 | NDV/PAA-907 [2.5] | 11 | 7 |
| 4 | NDV/PAA-934PH [2.5] | 10 | 3 |
| 5 | NDV/Al(OH)$_3$ [2.5] | 6 | 3 |
| 6 | NDV/Liposomes [0.5] | 51 | 36 |
| 7 | NDV/CTB [0.5] | 62 | 65 |
| IgA in the spleen | | | |
| 1 | NDV/None [0] | 8 | 3 |
| 2 | NDV/BUTYL-PAA [2.5] | 40 | 5 |

[mg/ml] is mg of adjuvant/ml of adjuvant solution

EXAMPLE 12

Effects of BUTYL-PAA, PAA-907, PAA-934PH and Al(OH)$_3$ on Numbers of Anti-NDV IgA-producing Cells in Lung and Spleen Cell Suspensions Part 1: Preparation of Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 9.

PAA-907 (CARBOPOL-907; BFGoodrich) and the adjuvant formulations thereof were prepared as described above in Example 6 having the concentrations of the PAA-907 adjuvant set forth below in Table 9.

PAA-934PH (CARBOPOL-934PH; BFGoodrich) and the adjuvant formulations thereof and Al(OH)$_3$ (SUPERFOS) and the adjuvant formulations thereof were all prepared as described above in Example 9 having the concentrations of the PAA-934PH adjuvant or the Al(OH)$_3$ adjuvant, set forth below in Table 9.

Part 2: Preparation of the Vaccine Formulations

The Newcastle Disease Virus stock antigen solution and the various vaccine formulations were prepared as described above in Example 4.

Part 3: Immunization of the Specimens

Sixty female mice (NMRI, Charles River, Germany) were obtained and divided into ten groups of six specimens per group.

On day 0, the specimens of each of the ten groups were narcotized slightly with ether.

Each of the specimens of two groups (Group 1 and Group 2) were then administered respective 40 µl doses containing a mixture of 20 µl of the pure NDV stock antigen solution and 20 µl of phosphate buffer pH=7.5 (described above) by dropping 20 µl of this mixture in each nostril of each specimen.

Each of the specimens of the remaining eight groups (Groups 3, 4, 5, 6, 7, 8, 9 and 10) were then immunized intranasally with respective 40 µl doses of the vaccine formulations (antigen/adjuvant mixtures containing 20 µl of the antigen solution and 20 µl of a particular adjuvant formulation), as specified below in Table 9, by dropping 20 µl of the mixture in each nostril of each specimen.

Administration of either the pure NDV stock antigen solution (to the specimens of Group 1 and of Group 2) or the antigen/adjuvant vaccine formulations (to the specimens of Groups 3–10) was repeated on day 14 with the same mixture and using the same protocol as described above for day 0.

Part 4: Preparation of Cell Suspensions

On day 21 (week 3) the specimens of five of the groups (Groups 1, 3, 5, 7 and 9) were again narcotized with ether and as much blood as possible was collected from each venus plexus thereof.

The specimens of these five groups (Groups 1, 3, 5, 7 and 9) were then sacrificed by cervical dislocation and the lungs thereof were carefully removed, so as to avoid the entrance of blood therein.

In the case of the specimens of Group 1 and Group 3 (as specified in Table 9 below), the spleens thereof were also removed.

Cell suspensions of the lung and spleen cells were then prepared as described above in Example 4.

On day 28 (week 4) the specimens of the other five groups (Groups 2, 4, 6, 8 and 10) were again narcotized with ether and as much blood as possible was collected from each venus plexus thereof.

The specimens of these five groups (Groups 2, 4, 6, 8 and 10) were then sacrificed by cervical dislocation and the lungs thereof were carefully removed, so as to avoid entrance of blood therein.

In the case of the specimens of Group 2 and Group 4 (as specified in Table 9 below), the spleens thereof were also removed.

Cell suspensions of the lungs and spleens were then prepared as described above in Example 4.

Part 5: Determination of the Number of Antigen Specific IgA-producing Cells in the Cell Suspensions The determination of the number of antigen specific IgA-producing cells in the lung cell suspensions was performed as described above in Example 4, with the exception that the number of antigen specific IgA-producing cells in the lung cell suspensions of only two samples of Groups 6 and 8 were determined.

The determination of the number of antigen specific IgA-producing cells in the spleen cell suspensions was performed as described above in Example 4, with the exception that the number of antigen specific IgA-producing cells in the spleen cell suspensions of only two samples of Groups 14 were determined.

The results of such calculations are set forth below in Table 9.

TABLE 9

| Group | Antigen/Adjuvant [mg/ml] | anti-NDV Ig-producing cells 10⁶ cells: | | | |
|---|---|---|---|---|---|
| | | 3 weeks after immunization | | 4 weeks after immunization | |
| | | mean | SEM | mean | SEM |
| IgA in the lungs | | | | | |
| 1, 2 | NDV/None [0] | 3 | 3 | 1 | 1 |
| 3, 4 | NDV/BUTYL-PAA [2.5] | 100 | 63 | 80 | 84 |
| 5, 6 | NDV/PAA-907 [2.5] | 49 | 46 | 4 | 6 |
| 7, 8 | NDV/PAA-934PH [2.5] | 161 | 129 | 72 | 27 |
| 9, 10 | NDV/Al(OH)$_3$ [2.5] | 9 | 5 | 6 | 3 |
| IgA in the spleen | | | | | |
| 1, 2 | NDV/None [0] | 13 | 8 | 1 | 1 |
| 3, 4 | NDV/BUTYL-PAA [2.5] | 30 | 5 | 4 | 3 |

[mg/ml] is mg of adjuvant/ml of adjuvant solution

EXAMPLE 13

Effects of BUTYL-PAA and PAA-907 on Numbers of Anti-NDV IgA-producing Cells in Lung and Spleen Cell Suspensions Part 1: Preparation of the Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 10.

PAA-907 (CARBOPOL-907; BFGoodrich) and the adjuvant formulations thereof were prepared as described above in Example 6 having the concentrations of the PAA-907 adjuvant set forth below in Table 10.

Part 2: Preparation of the Vaccine Formulations

The Newcastle Disease Virus stock antigen solution and the various vaccine formulations were prepared as described above in Example 4.

Part 3: Immunization of the Specimens

Eighty-four female mice (NMRI, Charles River, Germany) were obtained and divided into fourteen groups of six specimens per group.

On day 0, the specimens of each of the fourteen groups were narcotized slightly with ether.

Each of the specimens of two groups (Group 1 and Group 2) were then administered respective 40 µl doses containing a mixture of 20 µl of the pure NDV stock antigen solution and 20 µl of phosphate buffer pH=7.5 (described above) by dropping 20 µl of this mixture in each nostril of each specimen.

Each of the specimens of the remaining sixteen groups (Groups 3, 4, 5, 6, 7, 8, 9, 10, 11, 12, 13 and 14) were then immunized intranasally with respective 40 µl doses of the vaccine formulations (antigen/adjuvant mixtures containing 20 µl of the stock antigen solution and 20 µl of a particular adjuvant formulation), as specified below in Table 10, by dropping 20 µl of the mixture in each nostril of each specimen.

Administration of either the pure NDV stock antigen solution (to the specimens of Group 1 and of Group 2) or the antigen/adjuvant vaccine formulations (to the specimens of Groups 3–14) was repeated on day 14 with the same mixture and using the same protocol as described above for day 0.

Part 4: Preparation of Cell Suspensions

On day 21 (week 3) the specimens of seven of the groups (Groups 1, 3, 5, 7, 9, 11 and 13) were again narcotized with ether and as much blood as possible was collected from each venus plexus thereof.

The specimens of these seven groups (Groups 1, 3, 5, 7, 9, 11 and 13) were then sacrificed by cervical dislocation and the lungs thereof were carefully removed, so as to avoid the entrance of blood therein.

In the case of the specimens of Group 1 and Group 3 (as specified in Table 10 below), the spleens thereof were also removed.

Cell suspensions of the lungs and spleens were then prepared as described above in Example 4.

On day 28 (week 4) the specimens of the other seven groups (Groups 2, 4, 6, 8, 10, 12 and 14) were again narcotized with ether and as much blood as possible was collected from each venus plexuses thereof.

The specimens of these seven groups (Groups 2, 4, 6, 8, 10, 12 and 14) were then sacrificed by cervical dislocation and the lungs thereof were carefully removed, so as to avoid the entrance of blood therein.

In the case of the specimens of Group 2 and Group 4 (as specified in Table 10 below), the spleens thereof were also removed.

Cell suspensions of the lungs and spleens were then prepared as described above in Example 4.

Part 5: Determination of the Number of Antigen Specific IgA-producing Cells in the Cells Suspensions The determination of the number of antigen specific IgA-producing cells in the lung cell suspensions was performed as described above in Example 4, with the exception that the number of antigen specific IgA-producing cells in the lung cell suspensions of only two samples of Groups 10 and 12 were determined.

The determination of the number of antigen specific IgA-producing cells in the spleen cell suspensions was performed as described above in Example 4, with the exception that the number of antigen specific IgA-producing cells in the spleen cell suspensions of three samples of only Groups 14 were determined.

The results of such calculations are set forth below in Table 10.

TABLE 10

| Group | Antigen/Adjuvant [mg/ml] | anti-NDV Ig-producing cells 10⁶ cells: | | | |
|---|---|---|---|---|---|
| | | 3 weeks after immunization | | 4 weeks after immunization | |
| | | mean | SEM | mean | SEM |
| IgA in the lungs | | | | | |
| 1, 2 | NDV/None [0] | 2 | 2 | 3 | 3 |
| 3, 4 | NDV/BUTYL-PAA [2.5] | 333 | 21 | 43 | 7 |
| 5, 6 | NDV/BUTYL-PAA [1.7] | 304 | 131 | 312 | 55 |
| 7, 8 | NDV/BUTYL-PAA [5.0] | 102 | 1 | 66 | 20 |

TABLE 10-continued

| | | anti-NDV Ig-producing cells $10^6$ cells: | | | |
|---|---|---|---|---|---|
| | | 3 weeks after immunization | | 4 weeks after immunization | |
| Group | Antigen/Adjuvant [mg/ml] | mean | SEM | mean | SEM |
| 9, 10 | NDV/PAA-907 [0.5] | 97 | 13 | 4 | 3 |
| | NDV/PAA-907 [1.7] | 640 | 67 | 78 | 0 |
| | NDV/PAA-907 [5.0] | 720 | 8 | 114 | 55 |
| IgA in the spleen | | | | | |
| 1, 2 | NDV/None [0] | 25 | 4 | 6 | 2 |
| 3, 4 | NDV/BUTYL-PAA [1.7] | 188 | 24 | 282 | 178 |

[mg/ml] is mg of adjuvant/ml of adjuvant solution

EXAMPLE 14

Effects of BUTYL-PAA and SL-CD/squalane/water on Numbers of Anti-NDV IgA-producing Cells in Lung and Spleen Cell Suspensions Part 1: Preparation of Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 11.

Sulpholipo-cyclodextrin/squalane/water (SL-CD/squalane/water) adjuvant formulations were prepared as described above in Example 5 having the concentrations of the SL-CD/squalane/water adjuvant set forth below in Table 11.

Part 2: Preparation of the Vaccine Formulations

The Newcastle Disease Virus stock antigen solution and the various vaccine formulations were prepared as described above in Example 4.

Part 3: Immunization of the Specimens

Seventy-two female mice (NMRI, Charles River, Germany) were obtained and divided into twelve groups of six specimens per group.

On day 0, the specimens of each of the twelve groups were narcotized slightly with ether.

Each of the specimens of four groups (Group 1, Group 2, Group 3 and Group 4) were then administered respective 40 µl containing a mixture of 20 µl doses of the pure NDV stock antigen solution and 20 µl of phosphate buffer pH=7.5 (described above) by dropping 20 µl of this mixture in each nostril of each specimen.

Each of the specimens of the remaining eight groups (Groups 5, 6, 7, 8, 9, 10, 11 and 12) were then immunized intranasally with respective 40 µl doses of the vaccine formulations (antigen/adjuvant mixtures containing 20 µl of the stock antigen solution and 20 µl of a particular adjuvant formulation), as specified below in Table 11, by dropping 20 µl of the mixture in each nostril of each specimen.

Administration of either the pure NDV vaccine formulation (to the specimens of Groups 1–4) or the antigen/adjuvant vaccine formulations (to the specimens of Groups 5–12) was repeated on day 14 with the same mixture and using the same protocol as described above for day 0.

Part 4: Preparation of Cell Suspensions

On day 21 (week 3) the specimens of three of the groups (Groups 1, 5 and 9) were again narcotized with ether and as much blood as possible was collected from each venus plexus thereof.

The specimens of these three groups (Groups 1, 5 and 9) were then sacrificed by cervical dislocation and the lungs thereof were carefully removed, so as to avoid the entrance of blood therein.

In the case of the specimens of Group 1 and Group 5 (as specified in Table 11 below), the spleens thereof were also removed.

Cell suspensions of the lungs and spleens were then prepared as described above in Example 4.

On day 28 (week 4) the specimens of three other groups (Groups 2, 6 and 10) were again narcotized with ether and as much blood as possible was collected from each venus plexus thereof.

The specimens of these three groups (Groups 2, 6 and 10) were then sacrificed by cervical dislocation and the lungs thereof were carefully removed, so as to avoid the entrance of blood therein.

In the case of the specimens of Group 2 and Group 6 (as specified in Table 11 below), the spleens thereof were also removed.

Cell suspensions of the lungs and spleens were then prepared as described above in Example 4.

On day 35 (week 5) the specimens of three other groups (Groups 3, 7 and 11) were again narcotized with ether and as much blood as possible was collected from each venus plexus thereof.

The specimens of these three groups (Groups 3, 7 and 11) were then sacrificed by cervical dislocation and the lungs thereof were carefully removed, so as to avoid the entrance of blood therein.

In the case of the specimens of Group 3 and Group 7 (as specified in Table 11 below), the spleens thereof were also removed.

Cell suspensions of the lungs and spleens were then prepared as described above in Example 4.

On day 49 (week 7) the specimens of three other groups (Groups 4, 8 and 12) were again narcotized with ether and as much blood as possible was collected from each venus plexus thereof.

The specimens of these three groups (Groups 4, 8 and 12) were then sacrificed by cervical dislocation and the lungs thereof were carefully removed, so as to avoid the entrance of blood therein.

In the case of the specimens of Group 4 and Group 9 (as specified in Table 11 below), the spleens thereof were also removed.

Cell suspensions of the lungs and spleens were then prepared as described above in Example 4.

Part 5: Determination of the Number of Antigen Specific IgA-producing Cells in the Cells Suspensions The determination of the number of antigen specific IgA-producing cells in the lung cells suspensions was performed as described above in Example 4.

The determination of the number of antigen specific IgA-producing cells in the spleen cell suspensions was performed as described above in Example 4, with the exception that the number of antigen specific IgA-producing cells in the spleen cell suspensions of three samples of only Groups 1–8 were determined.

The results of such calculations are set forth below in Table 11.

TABLE 11

| | | anti-NDV Ig-producing cells/10⁶ cells at | | | | | | |
| | | (weeks after immunization) | | | | | | |
| | | 3 weeks | | 4 weeks | | 5 weeks | | 7 weeks | |
| Group | Antigen/Adjuvant [mg/ml] | mean | SEM | mean | SEM | mean | SEM | mean | SEM |
|---|---|---|---|---|---|---|---|---|---|
| IgA in the lungs | | | | | | | | | |
| 1–4 | NDV/None [0] | 10 | 4 | 43 | 11 | 3 | 2 | 15 | 4 |
| 5–8 | NDV/BUTYL-PAA [2.5] | 248 | 33 | 170 | 59 | 30 | 10 | 58 | 59 |
| 9–12 | NDV/SL-CD/squalane/water [2.5] | 19 | 17 | 11 | 8 | 4 | 2 | 0 | 0 |
| IgA in the spleen | | | | | | | | | |
| 1–4 | NDV/None [0] | 20 | 2 | 30 | 7 | 4 | 2 | 6 | 3 |
| 5–8 | NDV/BUTYL-PAA [2.5] | 43 | 8 | 116 | 24 | 5 | 2 | 29 | 5 |

[mg/ml] is mg of adjuvant/ml of adjuvant solution

EXAMPLE 15

Effects of BUTYL-PAA and SL-CD/squalane/water on Numbers of Anti-NDV IgA-producing Cells in Lung and Spleen Cells Suspensions Part 1: Preparation of Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 12.

Sulpholipo-cyclodextrin/squalane/water (SL-CD/squalane/water) adjuvant formulations were prepared as described above in Example 5 having the concentrations of the SL-CD/squalane/water adjuvant set forth below in Table 12.

Part 2: Preparation of the Vaccine Formulations

The Newcastle Disease Virus stock antigen solution and the various vaccine formulations were prepared as described above in Example 4.

Part 3: Immunization of the Specimens

Eighteen female mice (NMRI, Charles River, Germany) were obtained and divided into three groups of six specimens per group.

On day 0, the specimens of each of the three groups were narcotized slightly with ether.

Each of the specimens of one group (Group 1) were then administered respective 40 µl doses containing a mixture of 20 µl of the pure NDV stock antigen solution and 20 µl of phosphate buffer pH=7.5 (described above) by dropping 20 µl of this mixture in each nostril of each specimen.

Each of the specimens of the remaining two groups (Group 2 and Group 3) were then immunized intranasally with respective 40 µl doses of the vaccine formulations (antigen/adjuvant mixtures containing 20 µl of the stock antigen solution and 20 µl of a particular adjuvant formulation), as specified below in Table 12, by dropping 20 µl of the mixture in each nostril of each specimen.

Administration of either the pure NDV stock antigen solution (to the specimens of Group 1) or the antigen/adjuvant vaccine formulations (to the specimens of Groups 2 and 3) was repeated on day 21 with the same mixture and using the same protocol as described above for day 0.

Part 4: Preparation of Cell Suspensions

On day 42 (week 6) the specimens of the three groups were again narcotized with ether and as much blood as possible was collected from each venus plexus thereof.

The specimens of these three groups were then sacrificed by cervical dislocation and the lungs thereof were carefully removed, so as to avoid the entrance of blood therein.

In the case of the specimens of Group 1 and Group 2 (as specified in Table 12 below), the spleens thereof were also removed.

Cell suspensions of the lungs and spleens were then prepared as described above in Example 4.

Part 5: Determination of the Number of Antigen Specific IgA-producing Cells in the Cells Suspensions The determination of the number of antigen specific IgA-producing cells in the lung cells suspensions was performed as described above in Example 4, with the exception that the number of antigen specific IgA-producing cells in the lung cell suspensions of only two samples of Group 1 were determined.

The determination of the number of antigen specific IgA-producing cells in the spleen cell suspensions was performed as described above in Example 4, with the exception that the number of antigen specific IgA-producing cells in the spleen cell suspensions of only two samples of Groups 1 and 2 were determined.

The results of such calculations are set forth below in Table 12.

TABLE 12

| | | anti-NDV Ig-producing cells/10⁶ cells 6 weeks following immunization | |
| Group | Antigen/Adjuvant [mg/ml] | mean | SEM |
|---|---|---|---|
| IgA in the lungs | | | |
| 1 | None/None [0] | 1 | 1 |
| 2 | NDV/BUTYL-PAA [2.5] | 138 | 12 |
| 3 | NDV/SL-CD/squalane/water [2.5] | 4 | 0 |
| IgA in the spleen | | | |
| 1 | None/None [0] | 3 | 1 |
| 2 | NDV/BUTYL-PAA [2.5] | 29 | 6 |

[mg/ml] is mg of adjuvant/ml of adjuvant solution

EXAMPLE 16

Effects of BUTYL-PAA and CTB on Numbers of Anti-NDV IgA-producing Cells in Lung and Spleen Cells Suspensions Part 1: Preparation of Adjuvant Formulations The butyl-ester of polyacrylic acid (BUTYL-PAA), synthesized as described above in Example 2, was prepared as described above in Example 4 to form the adjuvant formulations having the concentrations of the Butyl-PAA adjuvant set forth below in Table 13.

CTB and the adjuvant formulations thereof were prepared as described above in Example 4 having the concentrations of the CTB adjuvant set forth below in Table 13.

Part 2: Preparation of the Vaccine Formulations

The Newcastle Disease Virus stock antigen solution and the various vaccine formulations were prepared as described above in Example 4.

Part 3: Immunization of the Specimens

Eighteen female mice (NMRI, Charles River, Germany) were obtained and divided into three groups of six specimens per group.

On day 0, the specimens of each of the three groups were narcotized slightly with ether.

Each of the specimens of one group (Group 1) were then administered respective 40 µl doses containing a mixture of 20 µl of the pure NDV stock antigen solution and 20 µl of phosphate buffer pH=7.5 (described above) by dropping 20 µl of this mixture in each nostril of each specimen.

Each of the specimens of the remaining two groups (Group 2 and Group 3) were then immunized intranasally with respective 40 µl doses of the vaccine formulations (antigen/adjuvant mixtures containing 20 µl of the antigen solution and 20 µl of a particular adjuvant solution), as specified below in Table 13, by dropping 20 µl of the mixture in each nostril of each specimen.

Administration of either the pure NDV stock antigen solution (to the specimens of Group 1) or the antigen/adjuvant vaccine formulations (to the specimens of Groups 2 and 3) was repeated on day 21 with the same mixture and using the same protocol as described above for day 0.

Part 4: Preparation of Cell Suspensions

On day 42 (week 6) the specimens of the three groups were again narcotized with ether and as much blood as possible was collected from each venus plexuses thereof.

The specimens of these three groups were then sacrificed by cervical dislocation and the lungs thereof were carefully removed, so as to avoid the entrance of blood therein.

In the case of the specimens of Group 1 and Group 2 (as specified in Table 13 below), the spleens thereof were also removed.

Cell suspensions of the lungs and spleens were then prepared as described above in Example 4.

Part 5: Determination of the Number of Antigen Specific IgA-producing Cells in the Cells Suspensions The determination of the number of antigen specific IgA-producing cells in the lung cells suspensions was performed as described above in Example 4.

The determination of the number of antigen specific IgA-producing cells in the spleen cell suspensions was performed as described above in Example 4, with the exception that the number of antigen specific IgA-producing cells in the spleen cell suspensions of only two samples of Groups 1 and 2 were determined.

The results of such calculations are set forth below in Table 13.

TABLE 13

| Group | Antigen/Adjuvant [mg/ml] | anti-NDV Ig-producing cells/$10^6$ cells 6 weeks following immunization | |
|---|---|---|---|
| | | mean | SEM |
| IgA in the lungs | | | |
| 1 | NDV/None [0] | 1 | 0 |
| 2 | NDV/BUTYL-PAA [2.5] | 4181 | 2589 |
| 3 | NDV/CTB [0.5] | 23 | 16 |
| IgA in the spleen | | | |
| 1 | None/None [0] | 1 | 1 |
| 2 | NDV/BUTYL-PAA [2.5] | 13 | 3 |

[mg/ml] is mg of adjuvant/ml of adjuvant solution

EXAMPLE 17

Effects of BUTYL-PAA and Liposomes on Numbers of Anti-NDV IgA-producing Cells in Lung and Spleen Cells Suspensions Part 1: Preparation of Adjuvant Formulations The butyl-ester of polyacrylic acid (BUTYL-PAA), synthesized as described above in Example 2, was prepared as described above in Example 4 to form the adjuvant formulations thereof having the concentrations of the Butyl-PAA adjuvant set forth below in Table 14.

Liposome and the adjuvant formulations thereof were prepared as described above in Example 9 having the concentrations of the liposome adjuvant set forth below in Table 14.

Part 2: Preparation of the Vaccine Formulations

The Newcastle Disease Virus stock antigen solution and the various vaccine formulations were prepared as described above in Example 4.

Part 3: Immunization of the Specimens

Eighteen female mice (NMRI, Charles River, Germany) were obtained and divided into three groups of six specimens per group.

On day 0, the specimens of each of the three groups were narcotized slightly with ether.

Each of the specimens of Group 1 were then administered respective 40 µl doses containing a mixture of 20 µl of the pure NDV stock antigen solution and 20 µl of phosphate buffer pH=7.5 (described above) by dropping 20 µl of this mixture in each nostril of each specimen.

Each of the specimens of the remaining two groups (Group 2 and Group 3) were then immunized intranasally with respective 40 µl doses of the vaccine formulations (antigen/adjuvant mixtures containing 20 µl of the antigen solution and 20 µl of a particular adjuvant solution), as specified below in Table 14, by dropping 20 µl of the mixture in each nostril of each specimen.

Administration of either the pure NDV stock antigen solution (to the specimens of Group 1) or the antigen/adjuvant vaccine formulations (to the specimens of Group 2 and Group 3) was repeated on day 14 with the same mixture and using the same protocol as described above for day 0.

Part 4: Preparation of Cell Suspensions

On day 21 (week 3) the specimens of the three groups were again narcotized with ether and as much blood as possible was collected from each venus plexus thereof.

The specimens of these three groups were then sacrificed by cervical dislocation and the lungs thereof were carefully removed, so as to avoid the entrance of blood therein.

In the case of the specimens of Group 1 and Group 2 (as specified in Table 14 below), the spleens thereof were also removed.

Cell suspensions of the lungs and spleens were then prepared as described above in Example 4.

Part 5: Determination of the Number of Antigen Specific IgA-producing Cells in the Cells Suspensions The determination of the number of antigen specific IgA-producing cells in the lung cells suspensions was performed as described above in Example 4.

The determination of the number of antigen specific IgA-producing cells in the spleen cell suspensions was performed as described above in Example 4, with the exception that the number of antigen specific IgA-producing cells in the spleen cell suspensions of only two samples of Groups 1 and 2 were determined.

The results of such calculations are set forth below in Table 14.

TABLE 14

| Group | Antigen/Adjuvant [mg/ml] | anti-NDV Ig-producing cells/$10^6$ cells 3 weeks following immunization | |
|---|---|---|---|
| | | mean | SEM |
| IgA in the lungs | | | |
| 1 | NDV/None [0] | 23 | 13 |
| 2 | NDV/BUTYL-PAA [2.5] | 411 | 211 |
| 3 | NDV/Liposomes [85] | 23 | 50 |
| IgA in the spleen | | | |
| 1 | NDV/None [0] | 18 | 4 |
| 2 | NDV/BUTYL-PAA [2.5] | 58 | 5 |

[mg/ml] is mg of adjuvant/ml of adjuvant solution

EXAMPLE 18

Effects of BUTYL-PAA, PAA-907, PAA-934PH, Liposomes and CTB on Numbers of Anti-NDV IgA-producing Cells in Lung and Spleen Cells Suspensions Part 1: Preparation of Adjuvant Formulations The butyl-ester of polyacrylic acid (BUTYL-PAA), synthesized as described above in Example 2, was prepared as described above in Example 4 to form the adjuvant formulations thereof having the concentrations of the Butyl-PAA adjuvant set forth below in Table 15.

PAA-907 (CARBOPOL-907; BFGoodrich) adjuvant formulations were prepared as described above in Example 6 having the concentrations of the PAA-907 adjuvant set forth below in Table 15.

PAA-934PH (CARBOPOL-934PH; BFGoodrich) adjuvant formulations and Al(OH)$_3$ (SUPERFOS) adjuvant formulations were prepared as described above in Example 9 having the concentrations of the respective adjuvant therein set forth below in Table 15.

CTB and the adjuvant formulations thereof were prepared as described above in Example 4 having the concentrations of the CTB adjuvant set forth below in Table 15.

Liposome and the adjuvant formulations thereof were prepared as described above in Example 9 having the concentrations of the liposome adjuvant set forth below in Table 15.

Part 2: Preparation of the Vaccine Formulations

A purified, inactivated influenza virus, strain MRC-11, was obtained (SOLVAY DUPHAR, Weesp, The Netherlands) and was grown in embryonic eggs, purified by centrifugation on a sucrose gradient and inactivated by incubation with 0.05% (v/v) β-propiolactone plus 0.01% (w/v) thimerosal for 4 days at 4° C. and subsequently for 3 days at room temperature as described in Vaccine 12, 653–660 (1994).

A stock antigen solution was then prepared from the inactivated MRC-11 containing 50 μg of purified inactivated influenza virus strain MRC-11 hemagglutinin per ml phosphate buffer solution (pH=7.5).

The vaccine formulation to be used was then obtained by mixing 1 volume of antigen solution with 1 volume of adjuvant solution.

Part 3: Immunization of the Specimens

Thirty-six female mice (NMRI, Charles River, Germany) were obtained and divided into six groups of six specimens per group.

On day 0, the specimens of each of the six groups were narcotized slightly with ether.

Each of the specimens of Group 1 were then administered respective 40 μl doses containing a mixture of 20 μl of the pure MRC-11 stock antigen solution as described above and 20 μl of phosphate buffer pH=7.5 (described above) by dropping 20 μl of this mixture in each nostril of each specimen.

Each of the specimens of the remaining five groups (Groups 2–6) were then immunized intranasally with respective 40 μl doses of the vaccine formulations (antigen/adjuvant mixtures containing 20 μl of the antigen solution and 20 μl of a particular adjuvant solution) as specified below in Table 15 (which vaccine formulations were obtained as described above) by dropping 20 μl of the mixture in each nostril of each specimen.

Administration of either the pure MRC-11 stock antigen solution (to the specimens of Group 1) or the antigen/adjuvant vaccine formulations (to the specimens of Groups 2–6) was repeated on day 14 with the same mixture and using the same protocol as described above for day 0.

Part 4: Preparation of Cell Suspensions

On day 21 (week 3) the specimens of the six groups were again narcotized with ether and as much blood as possible was collected from each venus plexus thereof.

The specimens of these six groups were then sacrificed by cervical dislocation and the lungs thereof were carefully removed, so as to avoid the entrance of blood therein.

In the case of the specimens of Group 1 and Group 2 (as specified in Table 15 below), the spleens thereof were also removed.

Cell suspensions of the lungs and spleens were then prepared as described above in Example 4.

Part 5: Determination of the Number of Antigen Specific IgA-producing Cells in the Cells Suspensions The determination of the number of antigen specific IgA-producing cells in the lung cells suspensions was performed as described above in Example 4, with the exception that, the number of antigen specific IgA-producing cells in the lung cell suspensions of only two samples of Groups 1 were determined and that, for the ELISPOT, the plates were coated with 25 μg purified inactivated influenza virus strain MRC-11 per ml coating buffer.

The determination of the number of antigen specific IgA-producing cells in the spleen cell suspensions was performed as described above in Example 4, with the exception that the number of antigen specific IgA-producing cells in the spleen cell suspensions of only two samples of Groups 1 and 2 were determined and that, for the ELISPOT, the plates were coated with 25 µg purified inactivated influenza virus strain MRC-11 per ml coating buffer.

The results of such calculations are set forth below in Table 15.

TABLE 15

| Group | Antigen/Adjuvant [mg/ml] | anti-NDV Ig-producing cells/$10^6$ cells 3 weeks following immunization | |
|---|---|---|---|
| | | mean | SEM |
| IgA in the lungs | | | |
| 1 | MRC-11/None [0] | 1 | 2 |
| 2 | MRC-11/BUTYL-PAA [2.5] | 1943 | 837 |
| 3 | MRC-11/PAA-907 [2.5] | 379 | 360 |
| 4 | MRC-11/PAA-934PH [2.5] | 780 | 462 |
| 5 | MRC-11/Liposomes [85] | 1 | 1 |
| 6 | MRC-11/CTB [0.5] | 82 | 57 |
| IgA in the spleen | | | |
| 1 | MRC-11/None [0] | 0 | 0 |
| 2 | MRC-11/BUTYL-PAA [10] | 23 | 3 |

[mg/ml] is mg of adjuvant/ml of adjuvant solution

EXAMPLE 19

Effects of BUTYL-PAA and PAA-907 on Numbers of Anti-NDV IgA-producing Cells and Numbers of Anti-BSA IgA-producing Cells in Lung Cell Suspensions Part 1: Preparation of Adjuvant Formulations The butyl-ester of polyacrylic acid (BUTYL-PAA), synthesized as described above in Example 2, was prepared as described above in Example 4 to form the adjuvant formulations thereof having the concentrations of the Butyl-PAA adjuvant set forth below in Table 16.

PAA-907 (CARBOPOL-907; BFGoodrich) adjuvant formulations were prepared as described above in Example 6 having the concentrations of the PAA-907 adjuvant set forth below in Table 16.

Part 2: Preparation of the Vaccine Formulations

The Newcastle Disease Virus stock antigen solution and the various vaccine formulations were prepared as described above in Example 4.

Bovine serum albumin (BSA) (from BSA, Fraction V, SIGMA) was prepared by dissolving in PBS at a final concentration of 500 µg/ml.

Part 3: Immunization of the Specimens

Thirty-six female mice (NMRI, Charles River, Germany) were obtained and divided into six groups of six specimens per group.

On day 0, the specimens of each of the six groups were narcotized slightly with ether.

Each of the specimens of Group 1 were then administered respective 40 µl doses containing a mixture of 20 µl of the pure NDV stock antigen solution and 20 µl of phosphate buffer pH=7.5 (described above) by dropping 20 µl of this mixture in each nostril of each specimen.

Each of the specimens of Group 4 were then administered respective 40 µl doses of the pure BSA stock antigen solution by dropping 20 µl of the said stock antigen solution in each nostril.

Each of the specimens of the remaining four groups (Groups 2, 3, 5 and 6) were then immunized intranasally with 40 µl of the vaccine formulations (antigen/adjuvant mixtures containing 20 µl of a particular antigen solution and 20 µl of a particular adjuvant solution), as specified below in Table 16, by dropping 20 µl of the mixture in each nostril of each specimen.

Administration of either the pure vaccine formulation (to the specimens of Group 1 and Group 4) or the antigen/adjuvant vaccine formulations (to the specimens of Groups 2, 3, 5 and 6) was repeated on day 14 with the same mixture and using the same protocol as described above for day 0.

Part 4: Preparation of Cell Suspensions

On day 21 (week 3) the specimens of the six groups were again narcotized with ether and as much blood as possible was collected from each venus plexus thereof.

The specimens of these six groups were then sacrificed by cervical dislocation and the lungs thereof were carefully removed, so as to avoid the entrance of blood therein.

Cell suspensions of the lungs were then prepared as described above in Example 4.

Part 5: Determination of the Number of Antigen Specific IgA-producing Cells in the Cells Suspensions The determination of the number of antigen specific IgA-producing cells in the lung cells suspensions was performed as described above in Example 4, with the exception that, for the ELISPOT for the specimens of Groups 4, 5 and 6, the plates were coated with 25 µg of BSA per ml coating buffer.

The results of such calculations are set forth below in Table 16.

TABLE 16

| Group | Antigen/Adjuvant [mg/ml] | anti-NDV Ig-producing cells/$10^6$ cells 3 weeks following immunization | |
|---|---|---|---|
| | | mean | SEM |
| IgA in the lungs | | | |
| 1 | NDV/None [0] | 41 | 27 |
| 2 | NDV/BUTYL-PAA [2.5] | 635 | 103 |
| 3 | NDV/PAA-907 [2.5] | 189 | 140 |
| 4 | BSA/None [0] | 0 | 0 |
| 5 | BSA/BUTYL-PAA [2.5] | 117 | 108 |
| 6 | BSA/PAA-907 [2.5] | 8 | 8 |

[mg/ml] is mg of adjuvant/ml of adjuvant solution

EXAMPLE 20

Synthesis of poly(acrylate-co-acrylamidomethylpropanesulfonic acid) Copolymer (p(A-c -AMPS))

Two p(A-c-AMPS) copolymers were synthesized as described by Iliopoulos and Audebert in Macromolecules 24, 2566–2575 (1991). Briefly, monoacrylic acid (AA; Merck) and acrylamidomethylpropanesulphonic acid (AMPS; Merck) were dissolved in ultrapure water, pH was adjusted at 7.4 with 10 N NaOH solution and ultrapure water was added to final total monomer concentration of 2 M. Air was removed from the solution by passing through nitrogen for at least 20 min.$(NH_4)_2S_2O_8$ and $Na_2S_2O_5$ were added to final concentrations of 1.46 mM and 2.91 mM, respectively. The mixture was incubated for 2.25 at 24 ° C. or 3 h at 20° C. under nitrogen and continuous stirring. After incubation, an excess of methanol was added and the mixture was kept overnight at ambient temperature. The precipitate formed was recovered in a solution of 9 g NaCl per L ultrapure water and dialyzed (Spectro/Por; MWCO 12,000–14,000 D) at 4° C. until no monomers were detected in the diafiltrate (absorbance at 210 nm<0.1 absorption units) and then dialyzed (Spectro/Por; MWCO 12,000–14,000 D) against ultrapure water. The retentate was lyophilized and the copolymers was recovered as powder and stored at ambient temperature until use. The molecular weight of the polymers was determined by gel permeation chromatography on a Sephacryl S400 column (Pharmacia, Sweden) using polyacrylate polymers with MW of 5, 90, 450, 750, 1000 and 3000 kD (Aldrich) as standards and absorbance at 210 nm as detection system. The percentage of AMPS monomer in the copolymer obtained was determined by element analysis. Details of the preparation procedure of copolymers and of the copolymers obtained are set forth below in Table 17.

TABLE 17

Preparation of copolymer p(A-c-AMPS) #1 and #2 by copolymerisation of monoacrylic acid (AA) and acrylamidomethylpropanesulfonic acid (AMPS).

| # | AA (g) | AMPS (g) | incubation time (h) | incubation temp (° C.) | % AMPS | MW (kD) |
|---|---|---|---|---|---|---|
| 1 | 25.9 | 8.3 | 2.25 | 24 | 9 | 350 |
| 2 | 38.9 | 12.4 | 3 | 20 | 12 | 370 |

EXAMPLE 21

Synthesis of poly(acrylate-co-vinylsulfonate) Copolymer (p(A-c-VS))

A p(A-c-VS) copolymer was synthesized as described above for p(A-c-AMPS) in Example 20. Briefly, monoacrylic acid (AA; Merck) and vinylsulphonic acid sodium salt (VS; Fluka) were dissolved in ultrapure water, pH was adjusted at 7.4 with 10 N NaOH solution and ultrapure water was added to final total monomer concentration of 2 M. Air was removed by saturating the solution with nitrogen. $(NH_4)_2S_2O_8$ and $Na_2S_2O_5$ were added to final concentrations of 1.46 mM and 2.91 mM, respectively. The mixture was incubated for 6 h at 19° C. under nitrogen and continuous stirring. After incubation, an excess methanol was added and the mixture was kept overnight at ambient temperature. The precipitate formed was recovered in a solution of 9 g NaCl per L ultrapure water and dialyzed (Spectro/Por; MWCO 12,000–14,000 D) at 4° C. until no monomers were detected in the diafiltrate (absorbance at 210 nm<0.1 absorption units) and then dialyzed (Spectro/Por; MWCO 12,000–14,000 D) against ultrapure water. The retentate was lyophilized and the copolymer was recovered as powder and stored at ambient temperature until use. The molecular weight of the polymer was determined by gel permeation chromatography on a Sephacryl S400 column (Pharmacia, Sweden) using polyacrylate polymers with MW of 5, 90, 450, 750, 1000 and 3000 kD (Aldrich) as standards and absorbance at 210 nm as detection system. The percentage of VS monomer in the copolymer obtained was determined by element analysis. Details of the preparation procedure of the copolymer and of the copolymer are set forth below in Table 18.

TABLE 18

Preparation of copolymer p(A-c-VS) #3 by copolymerisation of monoacrylic acid (AA) and vinylsulphonic acid sodium salt (VS).

| # | AA (g) | VBS (g) | incubation time (h) | incubation temp (° C.) | % VS | MW (kD) |
|---|---|---|---|---|---|---|
| 3 | 34.6 | 47.9 | 6 | 19 | 33 | 300 |

EXAMPLE 22

Synthesis of p(A-c-VBS) Copolymers p(A-c-VBS) copolymers were synthesized as described above for p(A-c-AMPS) in Example 20. Briefly, monoacrylic acid (AA) and vinylbenzenesulphonic acid sodium salt (VBS) were dissolved in ultrapure water, pH was adjusted at 7.4 with 10 N NaOH solution and ultrapure water was added to final total monomer concentration of 2 M. The solutions of the two monomers were saturated with nitrogen for at least 20 min. $(NH_4)_2S_2O_8$ and $Na_2S_2O_5$ were added to final concentrations of 1.46 mM and 2.91 mM, respectively. The mixtures were incubated for 6 or 24 h at 20° C. under nitrogen and continuous stirring of the solution. After incubation, an excess of methanol was added and the mixtures were kept overnight at ambient temperature. The precipitates formed were recovered in a solution of 9 g NaCl per L ultrapure water and dialyzed (Spectro/Por; MWCO 12,000–14,000 D) at 4° C. until no monomers were detected in the diafiltrate (absorbance at 210 nm<0.1 absorption units) and then dialyzed (Spectro/Por; MWCO 12,000–14,000 D) against ultrapure water. The retentates were lyophilized and the copolymers were recovered as powder and stored at ambient temperature until use. The molecular weight of the polymers were determined by gel permeation chromatography on a Sephacryl S400 column (Pharmacia, Sweden) using polyacrylate polymers 5, 90, 450, 750, 1000 and 3000 kD (Aldrich) as standards and absorbance at 210 nm as detection system. The percentage of VBS monomer in the copolymer obtained was determined by element analysis. Details of the preparation procedure of the copolymers and of the coplymers obtained are set forth below in Table 19.

TABLE 19

Preparation of copolymer p(A-c-VBS) #4, #5, #6 and #8 by copolymerisation of monoacrylic acid (AA) and vinylbenzenesulphonic acid sodium salt (VBS).

| # | AA (g) | VBS (g) | incubation time (h) | incubation temp (° C.) | % VBS | MW (kD) |
|---|---|---|---|---|---|---|
| 4 | 34.6 | 24.7 | 24 | 20 | 55 | >800 |
| 5 | 34.6 | 24.7 | 24 | 20 | 63 | 400 |
| 6 | 34.6 | 24.7 | 6 | 20 | 73 | 400 |
| 8 | 41.1 | 6.2 | 24 | 20 | 19 | 433 |

EXAMPLE 23

Synthesis of p(A-c-VBS) Copolymers p(A-c-VBS) copolymers #10 to #18 were synthesized as described above for p(A-c-VBS) in Example 22 with the exception that incubation time was between 24 and 168 h, incubation temperature was 37° C., and copolymers were recovered by diafiltration over a 100 kD (UFP-100-E6, AGFiltration) and 10 kD (UFP-10-E6, AGFiltration) giving two fractions of polymers with MW>100 kD and 10–100 kD. The polymer were lyophilized and stored at ambient temperature until use. Details of the copolymers and their preparation procedure are set out in Table 20.

TABLE 20

Preparation of copolymer p(A-c-VBS) #11 to #18 by copolymerisation of monoacrylic acid (AA) and vinylbenzenesulphonic acid sodium salt (VBS).

| # | AA (g) | VBS (g) | incubation time (h) | incubation temp (° C.) | % VBS | MW* >100 kD | MW* 10–100 kD |
|---|---|---|---|---|---|---|---|
| 11 | 0 | 59.3 | 168 | 37 | ND | ND | ND |
| 12 | 72.5 | 59.3 | 120 | 37 | ND | ND | ND |
| 13 | 73.2 | 49.6 | 120 | 37 | ND | ND | ND |
| 14 | 72.7 | 39.6 | 120 | 37 | ND | ND | ND |
| 15 | 73.1 | 29.6 | 144 | 37 | ND | ND | ND |
| 16 | 72.6 | 20.0 | 144 | 37 | ND | ND | ND |
| 17 | 73.3 | 9.9 | 168 | 37 | ND | ND | ND |
| 18 | 72.6 | 0.0 | 24 | 37 | ND | ND | ND |

*Fractions obtained by diafiltration over 100 and 10 kD membrane.
ND = not determined.

EXAMPLE 24

Effects of BUTYL-PAA, p(A-c-VS) and p(A-c-VBS)Copolymers and Polystyrene Sulphonate (PSS) on Numbers of Anti-NDV IgA-producing Cells in Lung Cell Suspensions Part 1: Preparation of Adjuvant Formulations BUTYL-PAA, p(A-c-VS) and p(A-c-VBS) were synthesized and prepared as described above in Example 2, 21 and 22 to form the adjuvant formulations having the concentrations set forth below in Table 21.

Polystyrene sulphonate with MW of 6000 kD (PSS, Polyscience Inc.) was dissolved in phosphate buffer solution (pH=7.5) to form the adjuvant formulation having the concentration of the polymer set forth below in Table 21.

Part 2: Preparation of the Vaccine Formulations

The various vaccines formulations specified below in Table 21 were prepared as described above in Example 4. The phosphate buffer solution (pH=7.5) prepared as described in Example 4 was used as a control in the experiment below.

Part 3: Immunization of the Specimens

Thirty female mice (BALB/c, Charles River, Germany) were obtained, divided into five groups of six specimens per group and treated with the vaccines set out in Table 21, according to the methodology described in Example 4.

Part 4: Preparation of the Cell Suspensions

As described in Example 4.

Part 5: Determination of the Number of Antigen Specific IgA-producing Cells in the Cell Suspensions As described above in Example 4.

The results are set forth below in Table 21.

TABLE 21

| | | Adjuvant | specific Ig-producing cells/$10^6$ cells 3 wks following first immunization | |
|---|---|---|---|---|
| Group | Antigen | [mg/ml] | mean | SEM |
| IgA in the lungs | | | | |
| 1 | NDV | None | 54 | 38 |
| 2 | NDV | BUTYL-PAA [2.5] | 377 | 399 |
| 3 | NDV | p(A-c-VS) #3 [2.5] | 423 | 369 |
| 4 | NDV | p(A-c-VBS) #5 [2.5] | 1088 | 1097 |
| 5 | NDV | PSS [2.5] | 492 | 462 |

EXAMPLE 25

Effects of BUTYL-PAA, p(A-VS) and p(A-c-VBS) Copolymers and PSS on Numbers of Anti-NDV IgA-producing Cells in Lung Cell Suspensions Example 24 was repeated and the results are set forth below in Table 22.

TABLE 22

| | | Adjuvant | specific Ig-producing cells/$10^6$ cells 3 weeks following first immunization | |
|---|---|---|---|---|
| Group | Antigen | [mg/ml] | mean | SEM |
| IgA in the lungs | | | | |
| 1 | NDV | None | 36 | 33 |
| 2 | NDV | BUTYL-PAA [2.5] | 538 | 557 |
| 3 | NDV | p(A-c-VS) #3 [2.5] | 113 | 99 |
| 4 | NDV | p(A-c-VBS) #5 [2.5] | 8705 | 4510 |
| 5 | NDV | PSS [2.5] | 492 | 462 |

EXAMPLE 26

Effects of p(A-c-AMPS) Copolymers on Numbers of Anti-A/Swine IgA-producing Cells in Lung Cell Suspensions Part 1: Preparation of Adjuvant Formulations p(A-c-AMPS), synthesized as described above in Example 20 was dissolved in phosphate buffer solution (pH=7.5) to form the adjuvant formulation set forth below in Table 23.

Part 2: Preparation of the Vaccine Formulations

Antigen preparation A/Swine: influenza virus strain A/Swine, was grown in embryonic eggs, purified by centrifugation on a sucrose gradient and inactivated by incubation with 0.05% (v/v) beta-propiolactone plus 0.01% (w/v) thimerosal for 4 days at 4° C. and subsequently for 3 days at room temperature as described in Vaccine 12, 653–660 (1994). Antigen stock solution of 250 µg HA per ml was prepared. The various vaccines formulations, specified below in Table 23, were then prepared by mixing one volume of the respective adjuvant formulations, prepared as described above, with one volume of the stock A/Swine antigen solution. The phosphate buffer solution (pH=7.5) prepared as described in Example 4 was used as a control in the experiment below.

Part 3: Immunization of the Specimens

Thirty-six female mice (BALB/c, Charles River, Germany) were obtained and divided in 6 groups of six specimens per group and treated with the vaccines set out in Table 23, according to the methodology described in Example 4.

Part 4: Preparation of the Cell Suspensions

As described in Example 4.

Part 5: Determination of the Number of Antigen Specific IgA-producing Cells in the Cell Suspensions As described above in Example 4, with the exception that, for the ELISPOT the plates were coated with 50 µg of influenza strain A/Swine per ml coating buffer described in Example 4.

The results are set forth below in Table 23.

TABLE 23

| Group | Antigen [µg/ml] | Adjuvant [mg/ml] | specific Ig-producing cells/$10^6$ cells 3 weeks following first immunization | |
| --- | --- | --- | --- | --- |
| | | | mean | SEM |
| IgA in the lungs | | | | |
| 1 | A/Swine [250] | None | 18 | 20 |
| 2 | A/Swine [250] | p(A-c-AMPS) #1 [2.0] | 21 | 29 |
| 3 | A/Swine [250] | p(A-c-AMPS) #2 [2.0] | 49 | 48 |

EXAMPLE 27

Effects of p(A-c-VS) Copolymer, Dextransulphate (DXS) and PSS on Numbers of Anti-A/Swine IgA-producing Cells in Lung Cell Suspensions Part 1: Preparation of Adjuvant Formulations Butyl-PAA, p(A-c-VBS) and PSS were obtained as described above in Examples 4, 22 and 24 respectively.

Dextran sulfate with MW of 500 kD (DXS; Phamacia, Sweden) was dissolved in phosphate buffer solution (pH=7.5) to form the adjuvant formulation having the concentration of the polymer set forth below in Table 24.

Part 2: Preparation of the Vaccine Formulations

Stock A/Swine antigen solution prepared as described above in Example 26 was adjusted at final concentrations of of 50 µg HA per ml.

The various vaccines formulations, specified below in Table 24, were then prepared by mixing one volume of the respective adjuvant formulations, prepared as described above, with one volume of the stock A/Swine antigen solution described above.

The phosphate buffer solution (pH=7.5) prepared as described in Example 4 was used as a control in the experiment below.

Part 3: Immunization of the Specimens

Thirty-six female mice (BALB/c, Charles River, Germany) were obtained and divided into 6 groups of six specimens per group and treated with the vaccines set out in Table 21, according to the methodology described in Example 4.

Part 4: Preparation of the Cell Suspensions

As described in Example 4.

Part 5: Determination of the Number of Antigen Specific IgA-producing Cells in the Cell Suspensions As described above in Example 4, with the exception that, for the ELISPOT the plates were coated with 50 µg of influenza strain A/Swine per ml coating buffer described in Example 4.

The results are set forth below in Table 24.

TABLE 24

| Group | Antigen [µg/ml] | Adjuvant [mg/ml] | specific Ig-producing cells/$10^6$ cells 3 weeks following first immunization | |
| --- | --- | --- | --- | --- |
| | | | mean | SEM |
| IgA in the lungs | | | | |
| 1 | A/Swine [50] | None | 21 | 16 |
| 2 | A/Swine [50] | BUTYL-PAA [1.0] | 40 | 46 |
| 3 | A/Swine [50] | p(A-c-VS) #3 [1.0] | 74 | 41 |
| 4 | A/Swine [50] | p(A-c-VS) #3 [1.0] | 32 | 24 |
| 5 | A/Swine [50] | PSS [1.0] | 15 | 29 |
| 6 | A/Swine [50] | DXS [1.0] | 38 | 64 |

EXAMPLE 28

Effects of BUTYL-PAA on Numbers of Anti-A/Swine IgA-producing Cells in Lung Cell Suspensions Part 1: Preparation of Adjuvant Formulations BUTYL-PAA was synthesized and prepared as described above in Example 4 to form the adjuvant formulation having the concentration of BUTYL-PAA set forth below in Table 25.

Part 2: Preparation of the Vaccine Formulations

Stock A/Swine antigen solution prepared as described above in Example 26 was adjusted at final concentrations of 50, 150, and 500 µg HA per ml. The various vaccine formulations, specified below in Table 25, were then prepared by mixing one volume of the respective adjuvant formulation, prepared as described above, with one volume of either stock A/Swine antigen solution described above. The phosphate buffer solution (pH=7.5) prepared as described in Example 4 was used as a control in the experiment below.

Part 3: Immunization of the Specimens

Thirty-six female mice (BALB/c, Charles River, Germany) were obtained, divided into 6 groups of 6 specimens per group and treated with the vaccines set out in Table 25 according to the general methodology of Example 4.

Part 4: Preparation of the Cell Suspensions

As described in Example 4.

Part 5: Determination of the Number of Antigen Specific IgA-producing Cells in the Cell Suspensions As described in Example 4 except that the plates were coated with 50 µg of influenza strain A/Swine per ml coating buffer described in Example 4.

The results are set forth below in Table 25.

TABLE 25

| Group | Antigen [µg/ml] | Adjuvant [mg/ml] | specific Ig-producing cells/$10^6$ cells 3 weeks following first immunization | |
| --- | --- | --- | --- | --- |
| | | | mean | SEM |
| IgA in the lungs | | | | |
| 1 | A/Swine [500] | None | 143 | 217 |
| 2 | A/Swine [150] | None | 50 | 42 |
| 3 | A/Swine [50] | None | 13 | 18 |
| 4 | A/Swine [500] | BUTYL-PAA [1.0] | 157 | 172 |
| 5 | A/Swine [150] | BUTYL-PAA [1.0] | 245 | 285 |
| 6 | A/Swine [50] | BUTYL-PAA [1.0] | 40 | 42 |

EXAMPLE 29

Effects of BUTYL-PAA on Numbers of Anti-A/Swine IgA-producing Cells in Lung Cell Suspensions Part 1: Preparation of Adjuvant Formulations BUTYL-PAA was synthesized and prepared as described above in Example 4 to form the adjuvant formulation having the various concentrations set forth below in Table 26.

Part 2: Preparation of the Vaccine Formulations

The various vaccines formulations, specified below in Table 26, were then prepared by mixing one volume of the respective adjuvant formulations, prepared as described above, with one volume of the stock A/Swine antigen solution prepared as described above in Example 26. The phosphate buffer solution (pH=7.5) prepared as described in Example 4 was used as a control in the experiment below.

Part 3: Immunization of the Specimens

Twenty-four female mice (BALB/c, Charles River, Germany) were obtained, divided into four groups of six specimens per group, and treated with the vaccines set out in Table 26, according to the general methodology.

Part 4: Preparation of the Cell Suspensions

As described in Example 4.

Part 5: Determination of the Number of Antigen Specific IgA-producing Cells in the Cell Suspensions As described above in Example 4, with the exception that, for the ELISPOT the plates were coated with 50 $\mu$g of influenza strain A/Swine per ml coating buffer described in Example 4. The results are set forth below in Table 26.

TABLE 26

| Group | Antigen [$\mu$g/ml] | Adjuvant [mg/ml] | specific Ig-producing cells/$10^6$ cells 3 weeks following first immunization | |
|---|---|---|---|---|
| | | | mean | SEM |
| IgA in the lungs | | | | |
| 1 | A/Swine [250] | None | 441 | 421 |
| 2 | A/Swine [250] | BUTYL-PAA [1.0] | 932 | 447 |
| 3 | A/Swine [250] | BUTYL-PAA [1.5] | 1487 | 1118 |
| 4 | A/Swine [250] | BUTYL-PAA [2.0] | 1454 | 2127 |

EXAMPLE 30

Effects of BUTYL-PAA on Numbers of Anti-A/Texas IgA-producing Cells in Lung Cell Suspensions Part 1: Preparation of Adjuvant and Antigen Formulations BUTYL-PAA was synthesized and prepared as described above in Example 4 to form the adjuvant formulation having the concentration set forth below in Table 27. Antigen preparation A/Texas: influenza virus strain A/Texas (Texas), was grown in embryonic eggs, purified by centrifugation on a sucrose gradient and inactivated by incubation with 0.05% (v/v) beta-propiolactone plus 0.01% (w/v) thimerosal for 4 days at 4° C. and subsequently for 3 days at room temperature as described in Vaccine 12, 653–660 (1994). Haemagglutinin/neuraminidase (HA/NA) subunits of the virus were isolated from the virus by using detergent(s). An antigen stock solution of 250 $\mu$g HA per ml was prepared.

Part 2: Preparation of the Vaccine Formulations

The various vaccines formulations, specified below in Table 27, were then prepared by mixing one volume of the respective adjuvant formulations, prepared as described above, with one volume of the stock A/Texas antigen solution prepared as described above.

The phosphate buffer solution (pH=7.5) prepared as described in Example 4 was used as a control in the experiment below.

Part 3: Immunization of the Specimens

Twelve female mice (BALB/c, Charles River, Germany) were obtained, divided into two groups of six specimens per group and treated with the vaccines set out in Table 27, according to the general methodology of Example 4.

Part 4: Preparation of the Cell Suspensions

As described in Example 4.

Part 5: Determination of the Number of Antigen Specific IgA-producing Cells in the Cell Suspensions As described above in Example 4, with the exception that, for the ELISPOT the plates were coated with 50 $\mu$g of influenza strain A/Texas per ml coating buffer described in Example 4. The results are set forth below in Table 27.

TABLE 27

| Group | Antigen [$\mu$g/ml] | Adjuvant [mg/ml] | specific Ig-producing cells/$10^6$ cells 3 weeks following first immunization | |
|---|---|---|---|---|
| | | | mean | SEM |
| IgA in the lungs | | | | |
| 1 | A/Texas [250] | None | 0 | 0 |
| 2 | A/Texas [250] | BUTYL-PAA [2.0] | 1245 | 1315 |

EXAMPLE 31

Effects of BUTYL-PAA on Numbers of Anti-A/Texas IgA-producing Cells in Lung Cell Suspensions The experiment of Example 30 was repeated and the results are set forth below in Table 28.

TABLE 28

| Group | Antigen [$\mu$g/ml] | Adjuvant [mg/ml] | specific Ig-producing cells/$10^6$ cells 3 weeks following first immunization | |
|---|---|---|---|---|
| | | | mean | SEM |
| IgA in the lungs | | | | |
| 1 | A/Texas [250] | None | 0 | 0 |
| 2 | A/Texas [250] | BUTYL-PAA [2.0] | 4409 | 4489 |

EXAMPLE 32

Effects of BUTYL-PAA and p(A-c-VBS) Copolymers on Numbers of Anti-A/Texas IgA-producing Cells in Lung Cell Suspensions Part 1: Preparation of Adjuvant Formulations BUTYL-PAA and p(A-c-VS) were synthesized as described above in Examples 4 and 21 respectively and dissolved in phosphate buffer solution (pH=7.5) to form the adjuvant formulations having the concentrations set forth below in Table 29.

Part 2: Preparation of the Vaccine Formulations

The various vaccines formulations, specified below in Table 29, were then prepared by mixing one volume of the respective adjuvant formulations, prepared as described above, with one volume of the stock A/Texas antigen solution prepared as described above in Example 30.

The phosphate buffer solution (pH=7.5) prepared as described in Example 4 was used as a control in the experiment below.

Part 3: Immunization of the Specimens

Twenty-four female mice (BALB/c, Charles River, Germany) were obtained, divided into four groups of six specimens per group and treated with the vaccines set forth in Table 29, according to the general methodology of Example 4.

Part 4: Preparation of the Cell Suspensions

As described in Example 4.

Part 5: Determination of the Number of Antigen Specific IgA-producing Cells in the Cell Suspensions As described above in Example 4, with the exception that, for the ELISPOT the plates were coated with 50 μg of influenza strain A/Texas per ml coating buffer described in Example 4. The results are set forth below in Table 29.

TABLE 29

| | Antigen | Adjuvant | specific Ig-producing cells/10⁶ cells 3 weeks following first immunization | |
|---|---|---|---|---|
| Group | [μg/ml] | [mg/ml] | mean | SEM |
| IgA in the lungs | | | | |
| 1 | A/Texas [250] | None | 0 | 0 |
| 2 | A/Texas [250] | BUTYL-PAA [2.0] | 431 | 559 |
| 3 | A/Texas [250] | p(A-c-VBS) #5 [2.0] | 664 | 1403 |
| 4 | A/Texas [250] | p(A-c-VBS) #6 [2.0] | 78 | 107 |

EXAMPLE 33

Effects of BUTYL-PAA and p(A-c-VBS) copolymers on Numbers of Anti-A/Texas IgA-producing Cells in Lung Cell Suspensions Preparation of Adjuvant Formulations Example 32 was repeated with two formulations of the p(A-c-VBS) copolymer adjuvant. The results are set forth below in Table 30.

TABLE 30

| | Antigen | Adjuvant | specific Ig-producing cells/10⁶ cells 3 weeks following first immunization | |
|---|---|---|---|---|
| Group | [μg/ml] | [mg/ml] | mean | SEM |
| IgA in the lungs | | | | |
| 1 | A/Texas [250] | None | 14 | 22 |
| 2 | A/Texas [250] | BUTYL-PAA [2.0] | 2014 | 2099 |
| 3 | A/Texas [250] | p(A-c-VBS) #5 [2.0] | 8784 | 13800 |

EXAMPLE 34

Effects of BUTYL-PAA, Dextransulphate (DXS) and Polystyrenesulphonate (PSS) on Numbers of Anti-A/Texas IgA-producing Cells in Lung Cell Suspensions Part 1: Preparation of Adjuvant Formulations BUTYL-PAA, p(A-c-VBS), PSS, and DXS were synthesized as described above in Examples 4, 22, 24 and 27 respectivley to form the adjuvants having the concentrations set forth below in Table 31.

Part 2: Preparation of the Vaccine Formulations

The various vaccines formulations, specified below in Table 30, were then prepared by mixing one volume of the respective adjuvant formulations, prepared as described above, with one volume of the stock A/Texas antigen solution prepared as described above in Example 30. The phosphate buffer solution (pH=7.5) prepared as described in Example 4 was used as a control in the experiment below.

Part 3: Immunization of the Specimens

Twenty-four female mice (BALB/c, Charles River, Germany) were obtained, divided into four groups of six specimens per group and treated with the vaccines set forth in Table 31, according to the general methodology of Example 4.

Part 4: Preparation of the Cell Suspensions

As described in Example 4.

Part 5: Determination of the Number of Antigen Specific IgA-producing Cells in the Cell Suspensions As described in Example 4 with the exception that, for the Elispot the plates were coated with 50 μg of influenza strain A/Texas per ml coating buffer described in Example 4.

The results are set forth below in Table 31.

TABLE 31

| | Antigen | Adjuvant | specific Ig-producing cells/10⁶ cells 3 weeks following first immunization | |
|---|---|---|---|---|
| Group | [μg/ml] | [mg/ml] | mean | SEM |
| IgA in the lungs | | | | |
| 1 | A/Texas [250] | None | 3 | 8 |
| 2 | A/Texas [250] | BUTYL-PAA [2.0] | 9179 | 17420 |
| 3 | A/Texas [250] | DXS [2.0] | 6 | 7 |
| 4 | A/Texas [250] | PSS [2.0] | 1613 | 2225 |

EXAMPLE 35

Effects of Butyl-PAA and Various p(A-c-VBS) Copolymers on Numbers of Anti-A/Texas IgA-producing Cells in Lung Cell Suspensions Part 1: Preparation of Adjuvant Formulations BUTYL-PAA and p(A-c-VBS) copolymers were synthesized as described above in Example 4 and 23, to form the adjuvant formulations having the concentrations set forth below in Table 32.

Part 2: Preparation of the Vaccine Formulations

The various vaccines formulations, specified below in Table 32, were then prepared by mixing one volume of the respective adjuvant formulations, prepared as described above, with one volume of the stock A/Texas antigen solution prepared as described in Example 30. The phosphate buffer solution (pH=7.5) prepared as described in Example 4 was used as a control in the experiment below.

Part 3: Immunization of the Specimens

Forty eight female mice (BALB/c, Charles River, Germany) were obtained, divided into 6 groups of six specimens per group and treated with the vaccines set forth in Table 32, according to the general methodology of Example 4.

Part 4: Preparation of the Cell Suspensions

As described in Example 4.

Part 5: Determination of the Number of Antigen Specific IgA-producing Cells in the Cell Suspensions As described in Example 4, with the exception that, for the ELISPOT the plates were coated with 50 μg of influenza strain A/Texas per ml coating buffer described in Example 4. The results are set forth below in Table 32.

TABLE 32

| | | | specific Ig-producing cells/$10^6$ cells 3 weeks following first immunization | |
|---|---|---|---|---|
| | Antigen | Adjuvant | | |
| Group | [μg/ml] | [mg/ml] | mean | SEM |
| IgA in the lungs | | | | |
| 1 | A/Texas [250] | None | 12 | 27 |
| 2 | A/Texas [250] | BUTYL-PAA [2.0] | 16887 | 24708 |
| 3 | A/Texas [250] | p(A-c-VBS) #13a [2.0] | 14443 | 22667 |
| 4 | A/Texas [250] | p(A-c-VBS) #14a [2.0] | 4319 | 4080 |
| 5 | A/Texas [250] | p(A-c-VBS) #15a [2.0] | 5642 | 6438 |
| 6 | A/Texas [250] | p(A-c-VBS) #16a [2.0] | 2923 | 2870 |
| 7 | A/Texas [250] | p(A-c-VBS) #17a [2.0] | 2629 | 2135 |
| 8 | A/Texas [250] | p(A-c-VBS) #18a [2.0] | 135 | 123 |

EXAMPLE 36

Effects of Butyl-PAA and Various p(A-c-VBS) Copolymers on Numbers of Anti-A/Texas IgA-producing Cells in Lung Cell Suspensions Part 1: Preparation of Adjuvant Formulations BUTYL-PAA and p(A-c-VBS) copolymers were synthesized as described above in Example 4 and 23, to form the adjuvant formulations having the concentrations set forth below in Table 33. The two fractions with MW of 10–100 and>100 kD of p(A-c-VBS) copolymers #12, #13, and #16, synthesized and purified as described above in Example 23, were dissolved in phosphate buffer solution (pH=7.5) to form the adjuvant formulation having the concentration of p(A-c-VBS) adjuvant set forth below in Table 33.

Part 2: Preparation of the Vaccine Formulations

The various vaccines formulations, specified below in Table 33, were then prepared by mixing one volume of the respective adjuvant formulations, prepared as described above, with one volume of the stock A/Texas antigen solution prepared as described in Example 30. The phosphate buffer solution (pH=7.5) prepared as described in Example 4 was used as a control in the experiment below.

Part 3: Immunization of the Specimens

Forty eight female mice (BALB/c, Charles River, Germany) were obtained, divided into 6 groups of six specimens per group and treated with vaccines as set out in Table 33, according to the general methodology of Example 4.

Part 4: Preparation of the Cell Suspensions

As described in Example 4.

Part 5: Determination of the Number of Antigen Specific IgA-producing Cells in the Cell Suspensions As described above in Example 4, with the exception that, for the ELISPOT the plates were coated with 50 μg of influenza strain A/Texas per ml coating buffer described in Example 4. The results are set forth below in Table 33.

TABLE 33

| | | | specific Ig-producing cells/$10^6$ cells 3 weeks following first immunization | |
|---|---|---|---|---|
| | Antigen | Adjuvant | | |
| Group | [μg/ml] | [mg/ml] | mean | SEM |
| IgA in the lungs | | | | |
| 1 | A/Texas [250] | None | 6 | 16 |
| 2 | A/Texas [250] | BUTYL-PAA [2.0] | 6417 | 7783 |
| 3 | A/Texas [250] | p(A-c-VBS) #12 10–100 kD [2.0] | 223 | 390 |
| 4 | A/Texas [250] | p(A-c-VBS) #13 10–100 kD [2.0] | 1139 | 1474 |
| 5 | A/Texas [250] | p(A-c-VBS) #16 10–100 kD [2.0] | 55 | 99 |
| 6 | A/Texas [250] | p(A-c-VBS) #12 > 100 kD [2.0] | 20796 | 25319 |
| 7 | A/Texas [250] | p(A-c-VBS) #13 > 100 kD [2.0] | 12219 | 20102 |
| 8 | A/Texas [250] | p(A-c-VBS) #16 > 100 kD [2.0] | 6530 | 7593 |

EXAMPLE 37

Effects of BUTYL-PAA and p(A-c-VBS) Copolymer #5 on Numbers of Anti-A/Texas IgA-producing Cells in Lung Cell Suspensions Part 1: Preparation of Adjuvant Formulations BUTYL-PAA and p(A-c-VBS) copolymer #5, were synthesized and prepared as described above in Example 4 and 22, to form the adjuvant formulations having the concentrations set forth below in Table 34.

Part 2: Preparation of the Vaccine Formulations

The various vaccines formulations, specified below in Table 34, were then prepared by mixing one volume of the respective adjuvant formulations, prepared as described above, with one volume of the stock A/Texas antigen solution prepared as described in Example 30. The phosphate buffer solution (pH=7.5) prepared as described in Example 4 was used as a control in the experiment below.

Part 3: Immunization of the Specimens

Eighteen female mice (BALB/c, Charles River, Germany) were obtained, divided into three groups of six specimens per group and treated with vaccines as set out below in Table 34, according to the general methodology of Example 4.

Part 4: Preparation of the Cell Suspensions

As described in Example 4.

Part 5: Determination of the Number of Antigen Specific IgA-producing Cells in the Cell Suspensions As described above in Example 4, with the exception that, for the ELISPOT the plates were coated with 50 μg of influenza strain A/Texas per ml coating buffer described in Example 4. The results are set forth below in Table 34.

TABLE 34

| | | | specific Ig-producing cells/$10^6$ cells 3 weeks following first immunization | |
|---|---|---|---|---|
| | Antigen | Adjuvant | | |
| Group | [μg/ml] | [mg/ml] | mean | SEM |
| IgA in the lungs | | | | |
| 1 | A/Texas [250] | None | 5 | 13 |
| 2 | A/Texas [250] | BUTYL-PAA [2.0] | 1747 | 1995 |
| 3 | A/Texas [250] | p(A-c-VBS) #5 [2.0] | 14951 | 15294 |

EXAMPLE 38

Effects of BUTYL-PAA and CTB on Numbers of Anti-A/Texas IgA-producing Cells in Lung Cell Suspensions Part 1: Preparation of Adjuvant Formulations BUTYL-PAA, synthesized as described above in Example 4, was dissolyed in phosphate buffer solution (pH=7.5) to form the adjuvant formulation set forth below in Table 35. CTB was dissolved in phosphate buffer solution (pH=7.5) to form the adjuvant formulation having the concentration of CTB set forth below in Table 34.

Part 2: Preparation of the Vaccine Formulations

The various vaccines formulations, specified below in Table 35, were then prepared by mixing one volume of the respective adjuvant formulations, prepared as described above, with one volume of the stock antigen solution. The phosphate buffer solution (pH=7.5) prepared as described in Example 4 was used as a control in the experiment below.

Part 3: Immunization of the Specimens

Eighteen female mice (BALB/c, Charles River, Germany) were obtained, divided into three groups of six specimens per group and treated with the vaccines set forth in Table 35, according to the general methodology of Example 4.

Part 4: Preparation of the Cell Suspensions

As described in Example 4.

Part 5: Determination of the Number of Antigen Specific IzA-producing Cells in the Cell Suspensions As described above in Example 4, with the exception that, for the ELISPOT the plates were coated with 50 µg of influenza strain A/Texas per ml coating buffer described in Example 4. The results are set forth below in Table 35.

TABLE 35

| Group | Antigen [µg/ml] | Adjuvant [mg/ml] | specific Ig-producing cells/$10^6$ cells 3 weeks following first immunization mean | SEM |
|---|---|---|---|---|
| IgA in the lungs | | | | |
| 1 | A/Texas [250] | None | 1 | 3 |
| 2 | A/Texas [250] | BUTYL-PAA [2.0] | 25437 | 24105 |
| 3 | A/Texas [250] | CTB [0.05] | 961 | 846 |

What is claimed is:

1. A method for inducing or enhancing mucosal immune responses to antigens comprising administering an antigen in conjunction with a water soluble polyanionic polymer mucosal adjuvant via a mucosal route, or administering an antigen separately from a water-soluble polyanionic polymer mucosal adjuvant wherein each said antigen and adjuvant are administered via a mucosal route, said adjuvant comprising a water-soluble polyanionic polymer having anionic constitutional repeating units, wherein the polyanionic polymer is a polyanionic heteropolymer, and further wherein the polyanionic heteropolymer contains two distinct anionic constitutional repeating units, wherein the units are selected from acrylic acid and either vinylsulphonic acid, vinylbenzenesulphonic acid, or acrylamidomethylpropanesulfonic acid.

2. The method of claim 1, wherein the polyanionic heteropolymer is a poly(acrylate-co-vinylsulfonate) copolymer.

3. The method of claim 1, wherein the polyanionic heteropolymer is a poly(acrylamidomethylpropanesulfonate) copolymer.

4. The method of claim 1, wherein the anionic constitutional repeating units are selected from the group consisting of acrylic acid and vinylbenzenesulphonic acid.

5. The method of claim 4, wherein the polyanionic polymer is a poly(acrylate-co-vinylbenzenesulfonate) copolymer.

6. A method of using a mucosal adjuvant for inducing or enhancing mucosal immune responses to antigens comprising administering an antigen in conjunction with a water soluble polyanionic polymer mucosal adjuvant via a mucosal route, or administering an antigen separately from a water-soluble polyanionic polymer mucosal adjuvant wherein each said antigen and adjuvant are administered via a mucosal route, said mucosal adjuvant comprising a water-soluble polyanionic polymer having anionic constitutional repeating units, wherein the anionic constitutional repeating units are obtained from one or more members selected from the group consisting of acrylic acid, methacrylic acid, maleic acid, fumaric acid, ethylsulphonic acid, vinylsulphuric acid, vinylsulphonic acid, styrenesulphonic acid, and acrylamidomethylpropanesulfonic acid, and salts of any of the foregoing, and further wherein the polyanionic polymer also comprises hydrophobic constitutional repeating units, wherein the units are obtained from one or more alkylesters selected from the group consisting of methyl-, ethyl-, propyl-, isopropyl-, n-butyl-, isobutyl-, secbutyl-, t-butyl-, n-hexyl-, n-octyl-, isooctyl-, 2-ethylhexyl-, n-decyl-, tetradecyl-, vinyl-, allyl- and oleylester, and further wherein the molar ratio of hydrophobic constitutional repeating units and anionic constitutional repeating units is between 0.02 and 0.6 hydrophobic constitutional repeating units per 1 anionic constitutional repeating unit.

7. The method of claim 6, wherein the molar ratio of hydrophobic constitutional repeating units and anionic constitutional repeating units is between 0.05 and 0.30 hydrophobic constitutional repeating units per 1 anionic constitutional repeating unit (from 5 to 30 hydrophobic constitutional repeating units per every 100 anionic constitutional repeating units).

8. The method of claim 6, wherein the hydrophobic constitutional repeating unit is n-butyl.

9. The method of claim 8, wherein the polyanionic polymer is n-butyl-polyacrylic acid polymer.

10. A method of inducing a mucosal response by mucosally administering a vaccine containing an antigen together with or separately with a mucosal adjuvant, said adjuvant comprising a water-soluble polyanionic polymer having anionic constitutional repeating units, wherein the anionic constitutional repeating units are obtained from one or more members selected from the group consisting of acrylic acid, methacrylic acid, maleic acid, fumaric acid, ethylsulphonic acid, vinylsulphuric acid, vinylsulphonic acid, styrenesulphonic acid, vinylphenylsulphuric acid, 2-methacryloyloxyethane sulphonic acid, 3-methacryloloxy-2-hydroxypropanesulphonic acid, 3-methacryl amido-3-methylbutanoic acid, acrylamidomethylpronesulfonic acid, vinylphosphoric acid, 4-vinylbenzoic acid, 3-vinyl oxypropane-1-sulphonic acid, N-vinylsuccinimidic acid, and salts of any of the foregoing, and further wherein the polyanionic polymer comprises hydrophobic constitutional repeating units, wherein the units are obtained from one or more members selected from the group consisting of alkylesters, cycloalkylesters, hydroalkylesters, ethers, glycols and aromatic groups and salts of any of the foregoing.

11. The method of claim 10, wherein the anionic constitutional repeating units are selected from the group consisting of acrylic acid, methacrylic acid, maleic acid, fumaric acid, ethylsulphonic acid, vinylsulphuric acid, vinylsulphonic acid styrenesulphonic acid, acrylamidomethylpropanesulfonic acid, and salts of any of the foregoing.

12. The method of claim 10, wherein the alkylesters are selected from the group consisting of methyl, ethyl, propyl, isopropyl, n-butyl, isobutyl, sec-butyl, t-butyl, n-hexyl, n-octyl, isooctyl-, 2-ethylhexyl, n-decyl, tetradecyl, vinyl, allyl and oleylester.

13. The method of claim 12, wherein the cycloalkylesters are selected from the group consisting of cyclohexyl, 1-methylcyclohexyl, 3-vinylcyclohexyl and 3,3,5-trimethylcyclohexylester.

14. The method of claim 10, wherein the molar ratio of hydrophobic constitutional repeating units and anionic constitutional repeating units of the polyanionic polymers is between 0 hydrophobic constitutional repeating units per 1 anionic constitutional repeating unit and 0.6 hydrophobic constitutional repeating units per 1 anionic constitutional repeating unit.

15. The method of claim 14, wherein the molar ratio of hydrophobic constitutional repeating units and anionic constitutional repeating units is between 0.02 and 0.60 hydrophobic constitutional repeating unit per 1 anionic constitutional repeating unit (from 2 to 60 hydrophobic constitutional repeating units per every 100 anionic constitutional repeating units).

16. The method of claim 15, wherein the molar ratio of hydrophobic constitutional repeating units and anionic constitutional repeating units is between 0.05 and 0.30 hydrophobic constitutional repeating unit per 1 anionic constitutional repeating unit (from 5 to 30 hydrophobic constitutional repeating units per every 100 anionic constitutional repeating units).

* * * * *